(12) United States Patent
Oberholzer et al.

(10) Patent No.: US 7,371,831 B2
(45) Date of Patent: May 13, 2008

(54) AZO DYESTUFFS

(75) Inventors: Martin Oberholzer, Therwil (CH); Jürgen Geiwiz, Lörrach (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 10/467,136

(22) PCT Filed: Feb. 11, 2002

(86) PCT No.: PCT/IB02/00398

§ 371 (c)(1),
(2), (4) Date: Jun. 16, 2006

(87) PCT Pub. No.: WO02/062902

PCT Pub. Date: Aug. 15, 2002

(65) Prior Publication Data

US 2004/0083924 A1    May 6, 2004

(30) Foreign Application Priority Data

Feb. 9, 2001    (GB) ................... 0103240.8

(51) Int. Cl.
C09B 35/50    (2006.01)
C09B 35/378    (2006.01)
C09D 11/00    (2006.01)

(52) U.S. Cl. ............... 534/606; 534/755; 534/796; 8/528; 8/639; 8/687; 8/693; 106/31.48; 560/49; 560/50

(58) Field of Classification Search ........... 534/606, 534/755, 796; 8/528, 639, 687, 693; 106/31.48
See application file for complete search history.

(56) References Cited

U.S. PATENT DOCUMENTS

| | | | |
|---|---|---|---|
| 3,211,717 A | 10/1965 | Thomas | |
| 3,817,940 A * | 6/1974 | Blahak et al. | ............. 528/68 |
| 3,971,741 A * | 7/1976 | Dehmel et al. | ............. 534/812 |
| 3,975,428 A * | 8/1976 | Blahak et al. | ............. 560/49 |
| 4,180,644 A * | 12/1979 | Marquis et al. | ............. 528/68 |
| 4,218,372 A | 8/1980 | Koerte | |
| 4,247,296 A | 1/1981 | Liedeck et al. | |
| 4,273,707 A | 6/1981 | Pedrazzi | |
| 4,363,761 A | 12/1982 | Pedrazzi | |
| 4,367,172 A | 1/1983 | Pedrazzi | |
| 4,764,175 A | 8/1988 | Dore et al. | |
| 5,493,011 A | 2/1996 | Jung et al. | |
| 5,929,215 A | 7/1999 | Pedrazzi | |
| 6,011,141 A | 1/2000 | Lamm et al. | |
| 6,015,885 A | 1/2000 | Ohta | |
| 6,048,968 A | 4/2000 | Etzbach et al. | |
| 6,297,362 B1 | 10/2001 | Kunde et al. | |
| 6,346,609 B1 * | 2/2002 | Etzbach et al. | ............. 534/608 |
| 2006/0117991 A1 * | 6/2006 | Mayo et al. | ............. 106/31.29 |

FOREIGN PATENT DOCUMENTS

| | | |
|---|---|---|
| DE | 2 002 816 | 7/1970 |
| DE | 2 001 748 | 8/1970 |
| DE | 29 15 323 | 11/1978 |
| DE | 36 25 576 | 2/1987 |
| EP | 0 855 387 | 7/1998 |
| EP | 0 955 342 | 11/1999 |
| FR | 2 147 312 | 3/1973 |
| FR | 2147312 * | 3/1973 |
| GB | 1 263 235 | 2/1972 |
| GB | 1 295 685 | 11/1972 |
| GB | 1 366 776 | 9/1974 |
| GB | 2 190 392 | 11/1987 |
| GB | 2 303 634 | 2/1997 |
| WO | WO 97/24405 | 7/1997 |

OTHER PUBLICATIONS

"Advanced Organic Chemistry", Fieser & Fieser, pp. 736-740.
PCT Search Report for application No. PCT/IB 02/00398, mail dated Jun. 18, 2002.
PCT International Preliminary Examination Report for PCT/IB 02/00398, mail dated May 22, 2003.

* cited by examiner

*Primary Examiner*—Fiona T Powers
(74) *Attorney, Agent, or Firm*—Tod A. Waldrop

(57) ABSTRACT

Compounds of formula (I)

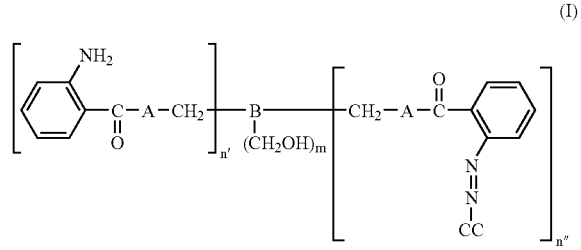

wherein all substituents have the meanings as defined in the Specification, their production and their use.

27 Claims, No Drawings

AZO DYESTUFFS

The present invention relates to novel azo or polyazo dyestuffs, their production, their use as well as to the novel amino compounds.

Various azo or polyazo dyestuffs as well as their production are already well known. The variety of such compounds is enormous. Recent patents or patents application dealing with polyazo dyestuffs and its starting products are U.S. Pat. No. 6,015,885, WO97/24405.

Azo or polyazo compounds can be used for dyeing or printing all kinds of fiber material like cellulose, cotton, keratinous fibers, for example hair, or leather, but in particular paper or paper products or else bast fibers such as hemp, flax, sisal, jute, coir or straw.

The present invention relates to compounds of formula (I)

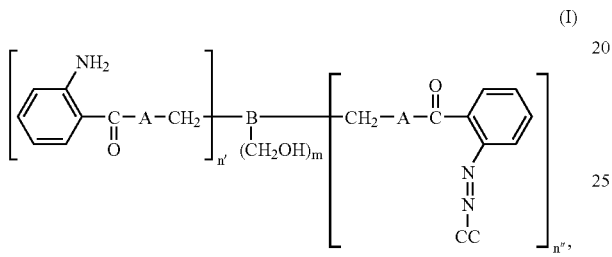

wherein
each A is independently —NH— or —O—,
B is a polyvalent group or atom,
n' and n" are natural numbers and the sum of n' and n" is $\geq 2$,
m is a natural number $\geq 0$,
CC is a moiety of formula (a)

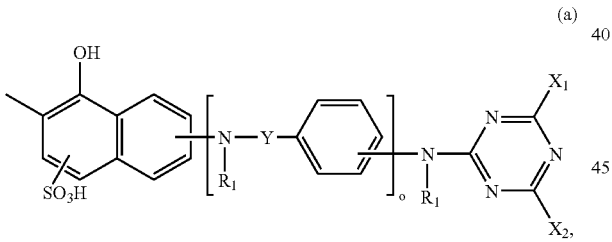

wherein
$R_1$ is H; $C_{1-4}$alkyl; $C_{1-4}$alkyl monosubstituted by hydroxy, halogen, cyano or $C_{1-4}$alkoxy,
$X_1$ and $X_2$ independently of each other are halogen; an aliphatic, cycloaliphatic, aromatic or heterocyclic amino group, said amino group comprising a protonatable nitrogen atom or a quaternary ammonium group, and being an aliphatic, cycloaliphatic, aromatic or heterocyclic mono($C_{1-4}$alkyl)-amino group, the $C_{1-4}$alkyl-group being unsubstituted or monosubstituted by halogen, $C_{1-4}$alkoxy, $C_{1-4}$alkyl, phenyl or hydroxy; an aliphatic, cycloaliphatic, aromatic or heterocyclic di($C_{1-4}$alkyl)-amino group, the $C_{1-4}$alkyl-groups being independently unsubstituted or monosubstituted by halogen, $C_{1-4}$alkyl, $C_{1-4}$alkoxy, phenyl or hydroxy; a $C_{5-6}$cycloalkylamino group, the cycloalkyl group being unsubstituted or substituted by one or two $C_{1-2}$alkyl groups; a phenylamino group, the phenyl ring being unsubstituted or substituted by one or two groups selected from halogen, $C_{1-4}$alkyl, $C_{1-4}$alkoxy, hydroxy and phenoxy; or a 5- or 6-membered ring containing one or two hetero atoms, in addition to N, O or S, which heterocyclic ring is unsubstituted or substituted by one or two $C_{1-4}$alkyl groups; or a group Z, where Z is independently selected from

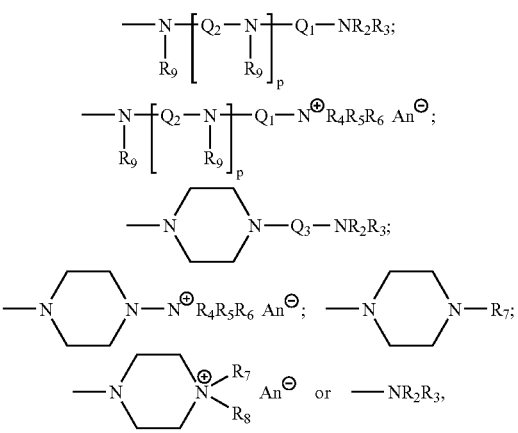

wherein
p is 0 or an integer 1, 2 or 3,
each $R_9$ is independently hydrogen; unsubstituted $C_{1-4}$alkyl or $C_{1-4}$alkyl monosubstituted by hydroxy, halogen, cyano or $C_{1-4}$alkoxy,
each $R_2$ and $R_3$ is independently hydrogen; unsubstituted $C_{1-6}$alkyl; $C_{2-6}$alkyl monosubstituted by hydroxy, amino or cyano; phenyl or phenyl-$C_{1-4}$alkyl, where the phenyl ring of the latter two groups is unsubstituted or substituted by one to three groups selected from chlorine, $C_{1-4}$alkyl, $C_{1-4}$alkoxy, unsubstituted $C_{5-6}$cycloalkyl or $C_{5-6}$cycloalkyl substituted by one to three $C_{1-4}$alkyl groups or a pyridinium ring, or
$R_2$ and $R_3$ together with the nitrogen atom to which they are attached, form a 5- or 6-membered ring containing one to three hetero atoms (in addition to N, one or two further N, O or S), which heterocyclic ring is unsubstituted or substituted by one or two $C_{1-4}$alkyl groups,
each $R_4$ and $R_5$ has independently one of significances of $R_2$ and $R_3$, except hydrogen,
$R_6$ is $C_{1-4}$alkyl or benzyl with the exception that $R_6$ is not benzyl when $R_4$ and $R_5$ have one of the cyclic significations of $R_2$ and $R_3$, or
$R_4$, $R_5$ and $R_6$ together with the nitrogen atom to which they are attached, form a pyridinium ring which is unsubstituted or substituted by one or two methyl groups,
$Q_1$ is $C_{2-8}$alkylene; $C_{3-6}$alkylene substituted by one or two hydroxy groups; $C_{1-6}$alkylene-1,3- or 1,4-phenylene, or —*NHCOCH$_2$, where * denotes the atom bound to —NR$_9$,
$Q_2$ is $C_{2-8}$alkylene; $C_{3-6}$alkylene substituted by one or two hydroxy groups; $C_{1-6}$alkylene-1,3- or -1,4-phenylene or 1,3- or 1,4-phenylene,
$Q_3$ is $C_{2-8}$alkylene,
$R_7$ is hydrogen; unsubstituted $C_{1-6}$alkyl or $C_{1-6}$alkyl monosubstituted by hydroxy, cyano, chlorine or phenyl, $R_8$ is unsubstituted $C_{1-6}$alkyl or $C_{1-6}$alkyl monosubstituted by hydroxy, cyano or chlorine, and $An^\ominus$ is a non-chromophoric anion, Y is direct bond, —CO— or —CO—NH—*, wherein the asterisk signifies the bond to the benzene ring and o is 0 or 1, or CC is a moiety of formula (b)

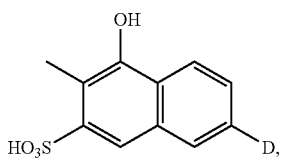

(b)

wherein

D is a basic group —$NR_1$-$Q_4$-$NR_2R_3$ or a cationic group —$NR_1$-$Q_4$-$N^+R_4R_5R_6$, in which $R_1$, $R_2$, $R_3$, $R_4$, $R_5$ and $R_6$ have the same meanings as above and $Q_4$ is $C_{2-6}$alkylene, which may be interrupted by —O—, —S— or —N($R_1$)—; $C_{2-3}$alkylene substituted by one or two hydroxy groups; or —*NHCOCH$_2$—, where * denotes the atom bound to the —$NR_1$-radical, or CC is a moiety of formula ($c_1$) or ($c_2$)

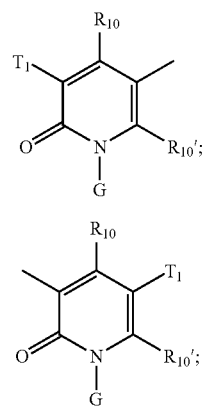

($c_1$)

($c_2$)

wherein each $R_{10}$ independently of each other is H; $C_{1-4}$alkyl; $C_{5-6}$cycloalkyl; phenyl, benzyl or phenylethyl, each $R_{10}'$ independently of each other is H; —OH or $C_{1-4}$alkyl each $T_1$ independently of each other are H; —CN; —$COOR_{15}$; $CONR_{16}R_{17}$; $SO_2NR_{16}R_{17}$;

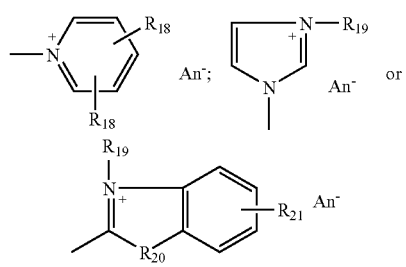

G is H; —$R_{11}NHR_{12}$ or —$R_{11}NR_{13}R_{14}$, wherein $R_{11}$ signifies $C_{1-6}$alkylene or $C_{2-6}$alkenylene, $R_{12}$ and $R_{13}$ independently of each other are H; unsubstituted $C_{1-6}$alkyl; $C_{2-6}$alkyl substituted by OH, CN or halogen; phenyl-$C_{1-3}$ alkyl, wherein the phenyl radical is optionally substituted from 1 to 3 times, by a substituent from the group of substituents comprising chlorine, $C_{1-4}$alkyl or $C_{1-4}$alkoxy; unsubstituted $C_{5-6}$cycloalkyl or $C_{5-6}$cycloalkyl substituted from 1 to 3 times by $C_{1-4}$alkyl groups, $R_{14}$ signifies any of the meanings of $R_{12}$ or $R_{13}$ or hydrogen, $R_{15}$ signifies a $C_{1-6}$alkyl radical or phenyl-$C_{1-3}$alkyl radical, $R_{16}$ and $R_{17}$ independently of each other are H or a $C_{1-4}$alkyl radical, $R_{18}$ independently of each other signifies H; a $C_{1-4}$alkyl radical; —$NR_{16}R_{17}$—$(CH_2)_{2-4}$—$NR_{16}R_{17}$ or —$CONR_{16}R_{17}$, $R_{19}$ signifies a $C_{1-4}$alkyl radical or a hydroxy-$C_{1-4}$alkyl radical, $R_{20}$ signifies —S— or —O—, $R_{21}$ signifies hydrogen or a $C_{1-4}$alkyl radical and $An^-$ is a non-chromophoric anion, with the provisos that (i) the sum of n', n" and m is smaller as or equal to the valencies of B, (ii) when the sum of n' and n"=2 then m is $\geq 1$, (iii) when the sum of n' and n"=3 and A=NH then m is $\geq 1$ and their salts and mixtures thereof.

In the compounds of formula (I) the anions $An^-$ can be any non-chromophoric anions such as those conventional in basic dyestuff chemistry. Suitable anions include chloride, bromide, sulphate, bisulphate, methylsulphate, aminosulphonate, perchlorate, benzenesulphonate, oxalate, maleate, acetate, propionate, lactate, succinate, tartrate, malate, methanesulphonate and benzoate as well as complex anions, for example zinc chloride double salts and anions of boric acid, citric acid, glycollic acid, diglycollic acid and adipic acid or addition products of ortho boric acids with polyalcohols with at least one cis diol group present. These anions can be exchanged for each other by ion exchange resins on reaction with acids or salts (for example via the hydroxide or bi-carbonate) or according to German Offenlegungsschrift 2,001,748 or 2,002,816.

In preferred compounds CC has the following formulae ($c_2$) or ($a_1$)

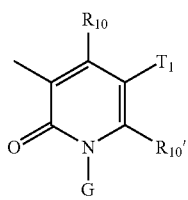

($c_2$)

wherein $R_{10}$ signifies H; —$CH_3$ or —$CH_2CH_3$, $T_1$ signifies H; —CN; —$CONH_2$; —$CONHCH_3$;

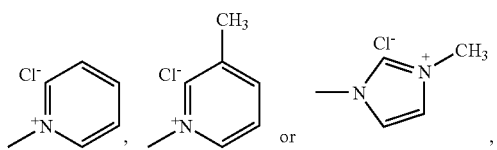

$R_{10}'$ signifies H; —CH$_3$ or —OH,
G signifies H or —(CH$_2$)$_{2-4}$NR$_{13}$R$_{14}$,
wherein
$R_{13}$ and $R_{14}$ are independently from each other H; —CH$_3$ or —CH$_2$CH$_3$, or

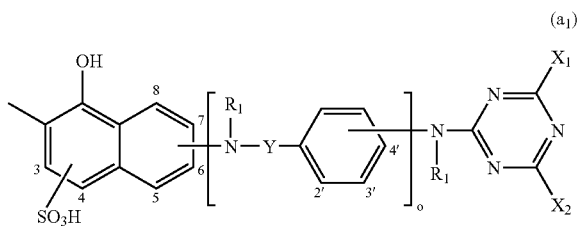

wherein
each $R_1$ is independently from each other H; —CH$_3$, —CH$_2$CH$_3$ or substituted C$_{1-4}$alkyl,
$X_1$ and $X_2$ are independently from each other halogen or —NR$_2$R$_3$, wherein $R_2$ and $R_3$ are independently from each other H; C$_{1-4}$alkyl; C$_{2-4}$alkylen-NH$_2$ or C$_{2-4}$alkylen-OH,
Y signifies a direct bond;

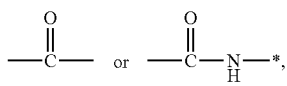

wherein the asterisk signifies the bond to the benzene ring and
o is 0 or 1.
If o is 0 then the NR$_1$-triazine group is preferably attached to the naphthol group at position 6 or 7.
If 0 is 1 then the NR$_1$-triazine group is preferably attached to the benzene ring at position 4' or 3' and to the naphthol group at position 6 or 7.
In further preferred compounds according to formula (I) B is a linear or branched alkylene group, wherein the number of carbon atoms goes from 1 to 25.
In further preferred compounds according to formula (I) B is a linear or branched alkylene group containing 2 to 40 carbon atoms, which is interrupted by at least one heteroatom choosing from the group of O, N and S, preferably O and/or S.
In more preferred compounds B is a group B' C[(CH$_2$)$_{0-4}$]$_{1-4}$.
In further more preferred compounds B is
[—(CH$_2$)$_{1-4}$—O—(CH$_2$)$_{1-4}$]$_4$C or
[—(CH$_2$)$_{1-3}$—O—(CH$_2$)$_{1-3}$—O—(CH$_2$)$_{1-3}$]$_4$C or
[—(CH$_2$)$_{1-2}$—O—(CH$_2$)$_{1-2}$—O—(CH$_2$)$_{1-2}$—O—(CH$_2$)$_{1-2}$]$_4$C or
[(—CH$_2$)$_{1-4}$]$_2$N(CH$_2$)$_{1-4}$N[(—CH$_2$)$_{1-4}$]$_2$.

Especially preferred compounds according to formula (I) have the formula (Ia),

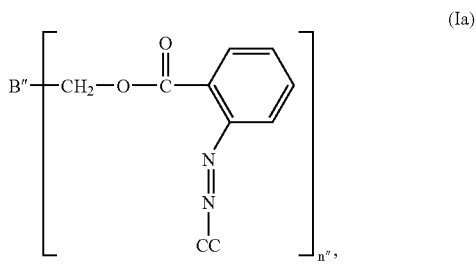

wherein
CC is a moiety of formula (a$_1$) or (c$_2$),
n" is 1, 2, 3 or 4,
with the provisos that
when n" is 1 then B" is C(CH$_2$OH)$_3$
when n" is 2 then B" is C(CH$_2$OH)$_2$
when n" is 3 then B" is; C(CH$_2$OH)
when n" is 4 then B" is C; [—(CH$_2$)$_{1-4}$—O—(CH$_2$)$_{1-4}$]$_4$C;
[—(CH$_2$)$_{1-3}$—O—(CH$_2$)$_{1-3}$—O—(CH$_2$)$_{1-3}$]$_4$C;
[—(CH$_2$)$_{1-2}$—O—(CH$_2$)$_{1-2}$—O—(CH$_2$)$_{1-2}$—O—(CH$_2$)$_{1-2}$]$_4$C or
[(—CH$_2$)$_{1-4}$]$_2$N(CH$_2$)$_{1-4}$N[(—CH$_2$)$_{1-4}$]$_2$.

A further embodiment of the present invention relates to mixtures of compounds comprising at least one compound of formula (I).

Preferred mixtures comprise at least one compound of formula (Ia) wherein B" is C(CH$_2$OH)$_3$ and n" is 1 and at least one compound of formula (Ia) wherein B" is C(CH$_2$OH)$_2$ and n" is 2 and at least one compound of formula (Ia) wherein B" is C(CH$_2$OH) and n" is 3 and at least one compound of formula (Ia) wherein B" is C and n" is 4.

Further preferred mixtures comprise at least one compound according to formula (I) (preferably formula (Ia)) or a mixture of compounds as described above and at least one compound of the examples 1-137 of the patent, GB 2190392A which is equivalent to U.S. Pat. No. 5,001,226 (issued Mar. 19, 1991), the entire contents of which is incoroorated herein by reference, and/or at least one C.I. Basic Red andlor at least one C.I. Basic Brown and/or at least one C.I. Basic Blue and/or at least one C.I. Basic Violet.

These preferred mixtures comprise from 2 to 98 parts (by weight) of at least one compound according to formula (I) (preferably formula (Ia)) or a mixture of compounds as described above as component one and at least one compound of the examples 1-137 of the patent GB 2190392A which is equivalent to U.S. Pat. No. 5,001,226 (issued Mar. 19, 1991), the entire contents of which is incorporated herein by reference, and/or at least one C.I. Basic Red and/or at least one C.I. Basic Brown and/or at least one C.I. Basic Blue and/or at least one C.I. Basic Violet in an amount to have 100 parts in total (e.g. from 98 to 2 parts) as component two. The mixtures may comprise component one and component two (component one/component two) in a ratio (by weight) of 2.0/98.0; 2.5/97.5; 12.5/87.5; 22.5/77.5; 32.5/67.5; 42.5/57.5; 50.0/50.0; 57.5/42.5; 67.5/32.5; 77.5/22.5; 80.0/20.0; 87.5/12.5; 90.0/10.0; 95.0/5.0; 97.5/2.5; or 98.0/2.0.

More preferred mixtures comprise mixtures of 10 to 50 parts of component one and 90 to 50 parts of component two.

Especially preferred mixtures comprise mixtures of 15 to 30 parts of component one and 85 to 70 parts of component two.

Especially preferred mixtures comprise mixtures comprise at least one compound of formula (Ia) and at least on C.I. Basic Brown 23 and/or C.I. Basic Red 12 and/or C.I. Basic Blue 1 and/or C.I. Basic Red 14 and/or C.I. Basic Violet 10 and/or C.I. Basic Blue 26.

A further embodiment of the present invention relates to novel amino compounds according to formula (II)

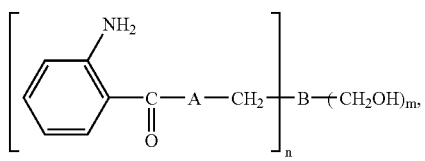

wherein
B signifies a linear or branched alkylene group, wherein the number of carbon atoms goes from 1 to 25 or a linear or branched alkylene group containing 2 to 40 carbon atoms, which is interrupted by at least one heteroatom choosing from the group of O, N and S, preferably O and/or S,
A signifies independently —NH— or —O—
m and n are natural numbers with the provisos that
(i) the sum of n and m is smaller as or equal to the valencies of B,
(ii) when n=2 then m is $\geq 1$,
(iii) when n=3 and A=NH then m is $\geq 1$, as well as to their salts and/or mixtures thereof.

In especially preferred compounds of formula (II) B is a group B' C[(CH$_2$)$_{0-4}$]$_{1-4}$.

In further especially preferred compounds of formula (II) B is
[—(CH$_2$)$_{1-4}$—O—(CH$_2$)$_{1-4}$]$_4$C or
[—(CH$_2$)$_{1-3}$—O—(CH$_2$)$_{1-3}$—O—(CH$_2$)$_{1-3}$]$_4$C or
[—(CH$_2$)$_{1-2}$—O—(CH$_2$)$_{1-2}$—O—(CH$_2$)$_{1-2}$
—O—(CH$_2$)$_{1-2}$]$_4$C or
[(—CH$_2$)$_{1-4}$]$_2$N(CH$_2$)$_{1-4}$N[(—CH$_2$)$_{1-4}$]$_2$.

A further aspect of this invention is the synthesis of the novel compounds according to formula (II), wherein compounds of formula (III)

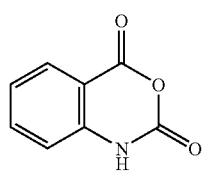

are reacted with a compound of formula (IVa) and/or a compound of formula (IVb)

B(CH$_2$OH)$_{m+n}$      (IVa)

B(CH$_2$NH$_2$)$_n$(CH$_2$OH)$_m$      (IVb)

wherein B, m and n are defined as above to a compound according to formula (II).

Preferably the reaction takes place in a common polar solvent. Such solvents are e.g. 1-methyl-2-pyrrolidinone or N,N-dimethyl-acetamide.

The temperature for this reaction is preferably between 40° C. and 70° C.

By the variation of the mole ratio between compound (III) and compound (IVa) and/or compound (IVb) and/or by the variation of the conditions of the reaction the value of n and m can be varied.

The compounds of formulae (III), (IVa) and (IVb) are known or may be produced in a manner familiar to the person skilled in the art.

Compounds according to formula (II) can be used as starting compounds in the production of compounds of formula (I).

The present process for the preparation of azo compounds (I) comprises reacting the diazonium salt of a compound according to formula (II) or mixtures of such diazonium salts with a suitable coupling component or with a mixture of suitable coupling components.

As coupling suitable component or as a mixture of suitable coupling components, any suitable coupling component and mixtures of suitable coupling components can be chosen. For example any suitable benzene, naphthalene or heterocyclic compound. Examples of suitable coupling components are listed e.g. in DE 3625576, DE 2915323, GB 2303634 and U.S. Pat. No. 5,929,215. Preferred coupling components comprise an optionally substituted pyridone group or a triazine group.

More preferred suitable coupling components comprise moieties of the formula CC wherein all substituents have the meanings as defined above. Even more preferred suitable coupling components comprise the formula (c$_2$) or (a$_1$).

Diazotization and coupling are effected by generally known processes.

The diazotization is carried out, for example using sodium nitrite in acid aqueous medium. The diazotization can also be carried out using other diazotization agents, for example nitrosulfuric acid. An additional acid may be present in the reaction medium during diazotization, for example phosphoric acid, sulfuric acid, acetic acid, propionic acid, hydrochloric acid or mixtures of these acids, e.g. mixtures of phosphoric acid and acetic acid. Diazotization is conveniently carried out in the temperature range of from −10° C. to 30° C., preferably from −10° C. to 20° C.

Coupling of the diazotised compound of formula (II) to the suitable coupling component, more specifically those components comprising moieties of formula CC or even more specifically those of comprising moieties of formula (c$_2$) or (a$_1$) is carried out in known manner, for example in acid, aqueous or aqueous-organic medium, preferably in the temperature range from −10° C. to 30° C., more preferably below 10° C. Acids used are, for example hydrochloric acid, acetic acid, sulfuric acid or phosphoric acid. Diazotization and coupling can for example be carried out in the same reaction medium.

Alkali metal nitrites, such as, for example, sodium nitrite, in solid form or as an aqueous, or in nitrosylsulfuric acid are employed as the nitrosating agents.

The preparation of the diazonium ion, typically through the reaction with excess nitrous acid or the like such as nitrosyl sulfuric at low temperature to form the electrophilic ion AN$_2^+$ is disclosed in the literature e.g. in "Advanced Organic Chemistry, Fieser & Fieser, pages 736-740" or in "Organische Chemie, K. Peter C. Vollhardt, pages 1154-1157, first edition (1. Auflage) 1988".

The coupling components comprising the moieties of formulae $(c_2)$ or $(a_1)$ are known or may be easily produced in a manner familiar to the person skilled in the art.

The compounds (or complexes) of formula (I) containing free basic groups may be converted wholly or in part into water-soluble salts by reacting with any one of the above-mentioned inorganic or organic acids.

The azo dyes according to formula (I) and the mixtures of these dyes can be used to dye or print all kind of fiber materials.

The azo compounds according to formula (I) or mixtures thereof, especially those comprising coupling components comprising the moieties of formula $(c_2)$ or $(a_1)$ are used in particular as dyes for dyeing and printing cationically dyeable substrates, such as wool, hair, silk, leather, acid-modified nylon materials, polyacrylonitrile materials, basically dyeable, modified polyester materials, natural and regenerated cellulose materials, such as cotton, hemp, flax, sisal, jute, coir or straw and viscose, on which these compounds have good affinity.

A preferred use of the azo dyes according to formula (I) and of mixtures of these dyes, especially those comprising coupling components comprising the formula $(c_2)$ or $(a_1)$ lies in the dyeing of paper of all kinds, especially bleached, unsized and sized lignin-free paper as well as wood containing paper or lignin containing paper.

A more preferred use of the azo dyes according to formula (I) and of mixtures of these dyes, especially those comprising coupling components of formula $(c_2)$ or $(a_1)$ lies in the dyeing of wood containing paper or lignin containing paper.

The novel dyes can be applied by a wide range of different processes to the paper material, e.g. in pulp dyeing, in the size press and from aqueous inks by the Ink Jet method.

Concentrated aqueous solutions of dyes of formula (I) can be prepared by filtering the dye suspension obtained in the synthesis of the dye, if appropriate effecting deionisation, conveniently by a membrane separation method, and stabilizing the solution by the addition of auxiliaries such as urea, ε-caprolactam or polyethylene glycol. It is, however, also possible to suspend the isolated dye in hydrochloric acid, to filter the dye suspension once more and to mix the filter cake with lithium hydroxide or a suitable amine, typically an alkanolamine, and the requisite amount of water. Finally, it is also possible to carry out the coupling in the presence of lithium hydroxide, ammonia or alkanolamine, and to deionise the synthesis solution.

For the preparation of inks for printing processes suitable organic solvents or mixtures thereof are used. E.g. alcohols, ethers, esters, nitriles, carbonacidamides, cyclic amides, urea, sulfones and sulfone oxides.

Furthermore additional auxiliaries such as e.g. buffers, viscosity improvers, surface tension improvers, fixation accelerants, biocides, corrosion inhibitors, leveling agents, drying agents, humefactants, ink penetration additives, light stabilizers, UV absorbers, optical brighteners, coagulation reducers, ionic or nonionic surfactants and conducting salts, may be added to the ink composition.

The fractions of the individual components of the ink compositions are 1-35 parts of a dye of the formula (I) and/or its salt or mixtures of various dyes of the formula (I), 65-99 parts of water or a medium including a mixture of water and an organic solvent, an anhydrous organic solvent or a solid having a low melting point and optionally and 0-5 parts of one or more additives. The total sum of all the parts of a composition according to the invention is 100 parts.

A further embodiment of the present invention are materials printed or dyed with compounds of formula (I) or mixtures thereof.

A further embodiment of the present invention are ink-jet inks comprising compounds according to formula (I) (preferably formula (Ia)) and/or mixtures comprising at least one compound according to formula (I) (preferably formula (Ia)) or a mixture of com-pounds as described above and at least one compound of the examples 1-137 of the patent GB 2190392A which is equivalent to U.S. Pat. No. 5,001,226 (issued Mar. 19, 1991) the entire contents of which is incorporated herein by reference, and/or at least one C.I. Basic Red and/or at least one C.I. Basic Brown and/or at least one C.I. Basic Blue and/or at least one C.I. Basic Violet, as well as a process for the preparation of this ink-jet inks by using this compounds and/or this mixtures.

The following examples further serve to illustrate the invention. In the Examples all parts and all percentages are by weight, and the temperatures given are in degrees Celsius, unless indicated to the contrary.

Syntheses of Bridged Anthranilic Acid Esters

EXAMPLE 1

65.3 parts isatoic anhydride are added slowly to a mixture of 13.6 parts pentaerytrite and 1.0 parts potassium carbonate in 50 parts 1-methyl-2-pyrrolidone at 50° C. The suspension is stirred for 2 hours and than diluted with 500 parts water. The resulting slurry is filtered, and the collected solid washed with water and dried in vacuum at 60° C. to obtain a white powder, having the formula (V)

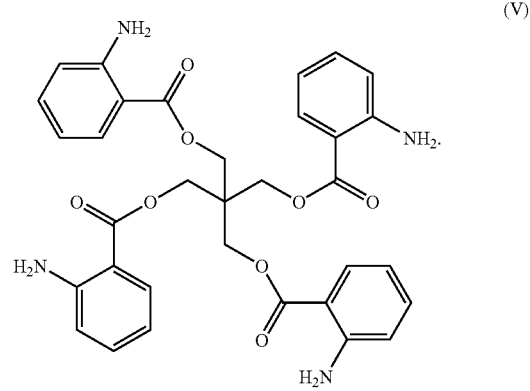

(V)

Example 1 could be also used for dyestuff synthesis without isolation.

EXAMPLE 2

49 parts isatoic anhydride are added slowly to a mixture of 13.6 parts pentaerytrite and 1.0 parts potassium carbonate in 50 parts N,N-dimethyl-acetamide at 50° C. The suspension is stirred for 2 hours and diluted with 500 parts water. The resulting slurry is filtered, and the obtained solid washed thoroughly with water and dried in vacuum at 60° C. to obtain a white powder, which is a mixture containing compounds having the formula (VIa, VIb, VIc, V)

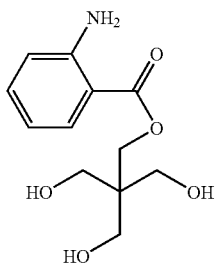
(VIa)

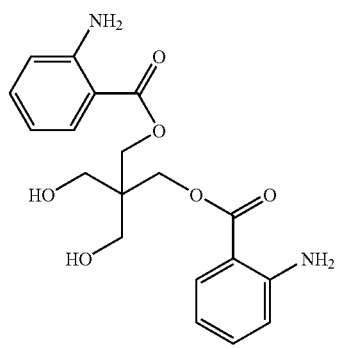
(VIb)

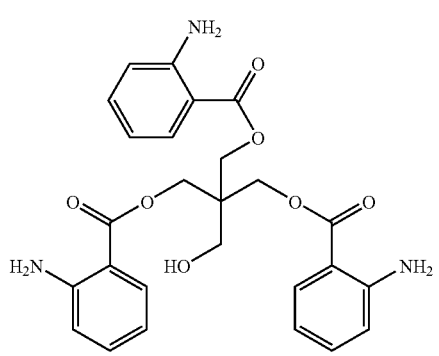
(VIc)

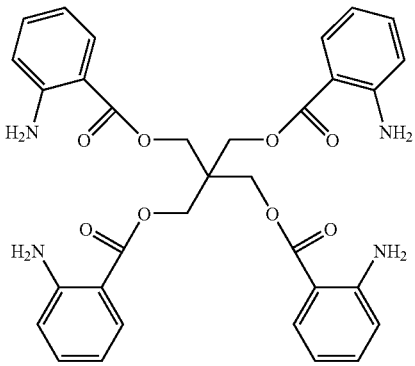
(V)

Further compounds of the general formula (IIa) may be produced analogously to the procedure given in Example 1 and 2.

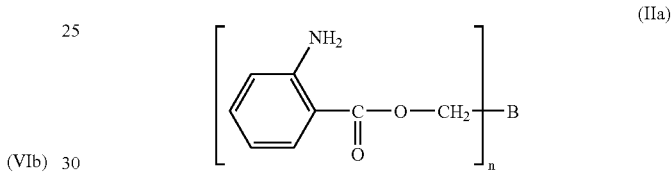
(IIa)

TABLE 1

EXAMPLES 3-7

| Ex. | B | n |
|---|---|---|
| 3 | (—CH$_2$—O—CH$_2$)$_4$C | 4 |
| 4 | (—CH$_2$—O—CH$_2$CH$_2$—O—CH$_2$CH$_2$—O—CH$_2$)$_4$C | 4 |
| 5 | —(CH$_2$CH$_2$—O—CH$_2$)$_4$C | 4 |
| 6 | (—CH$_2$CH$_2$)$_2$NCH$_2$CH$_2$N(CH$_2$CH$_2$—)$_2$ | 4 |
| 7 | 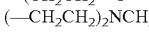 | 3 |

Syntheses of the Azo-Dyestuffs

EXAMPLE 8

60 parts of the amino-compound of Example 1 are dissolved in a mixture of 50 parts water, 120 parts 30% HCl and 60 parts acetic acid and diazotized at 0° C.-5° C. with 28 parts of a 4 N solution of sodium nitrite. 392 parts of a 20% solution of 6-hydroxy-4-methyl-1-(3'-methylamino)-propylpyridone-(2) in sulfuric acid are added to the diazo-solution. By the addition of 20 parts 30% sodium hydroxide solution and 150 parts ice the pH is adjusted to 2 at a temperature of 10° C.-20° C. After 1 hour stirring the pH is adjusted to 10 with 30% sodium hydroxide and the precipitated dyestuff is filtered off. A dyestuff of the following formula (VII)

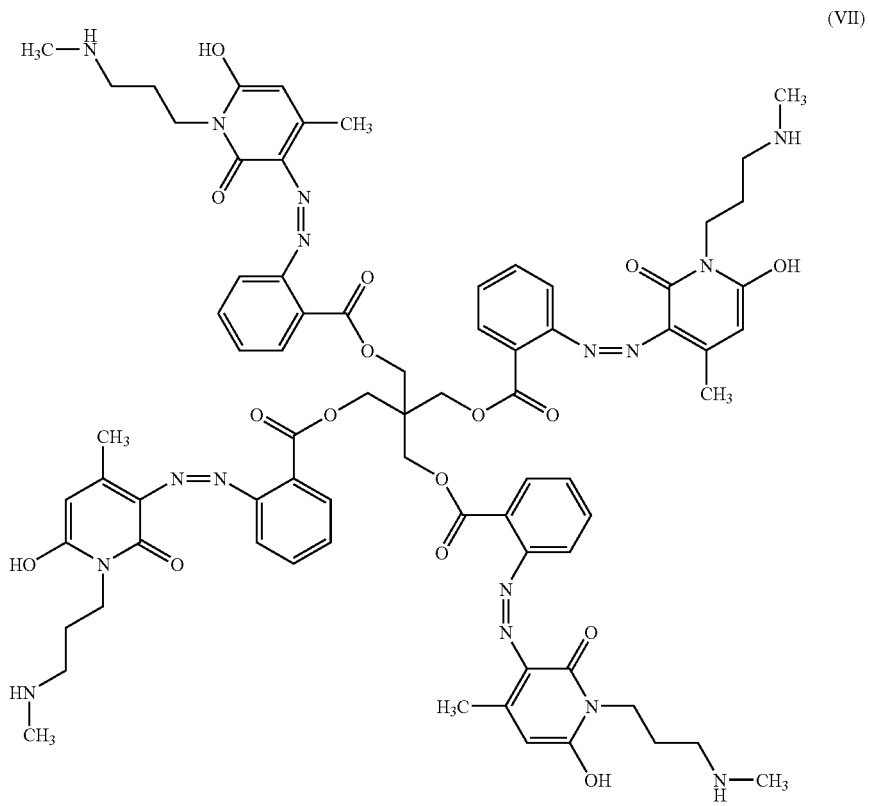

(VII)

is obtained.

The dyestuff is very soluble in diluted acids, particularly organic acids such as formic acid, lactic acid, acetic acid and methoxyacetic acid. The solution dyes paper in brilliant yellow shades. The obtained dye shows excellent wet fastness (against water, alcohol, milk, soapy water, sodium chloride solution, urine, etc.).

Further dyestuffs of the general formula (Ib) may be produced analogously to the procedure given in Example 8.

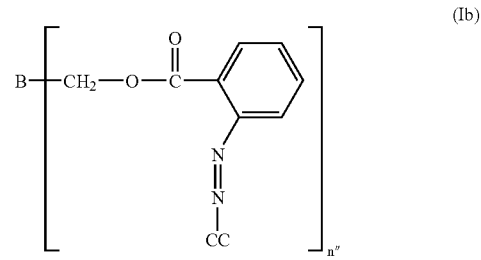

(Ib)

TABLE 2

EXAMPLES 9-34

| Ex. | B | n″ | CC | Shade |
|---|---|---|---|---|
| 9 | —C(CH₂—)₄ | 4 | (pyridinium-substituted methylpyridone, Cl⁻) | yellow |

TABLE 2-continued
EXAMPLES 9-34
| Ex. | B | n" | CC | Shade |
|---|---|---|---|---|
| 10 |  | 4 | 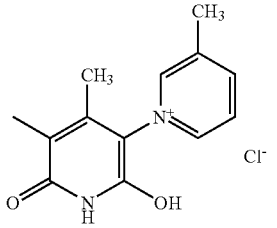 | yellow |
| 11 |  | 4 | 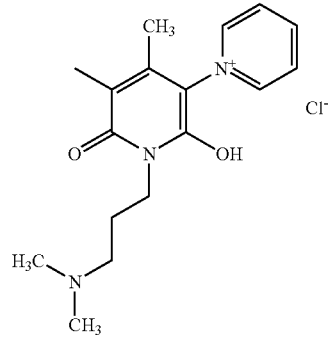 | yellow |
| 12 |  | 4 | 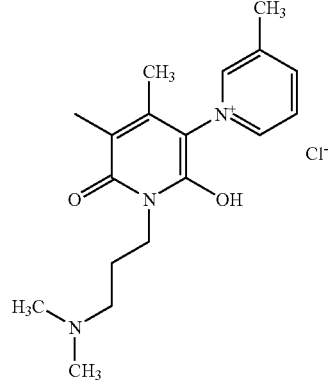 | yellow |

TABLE 2-continued

EXAMPLES 9-34

| Ex. | B | n" | CC | Shade |
|---|---|---|---|---|
| 13 | —C— (quaternary C) | 4 | pyridinone with CH$_3$, CH$_3$, OH, =O, N-(CH$_2$)$_3$-N(CH$_3$)$_2$ | yellow |
| 14 | —C— | 4 | pyridinone with CH$_3$, CH$_3$, CN, OH, =O, N-(CH$_2$)$_3$-N(CH$_3$)$_2$ | yellow |
| 15 | —C— | 4 | pyridinone with CH$_3$, CH$_3$, CONH$_2$, OH, =O, N-(CH$_2$)$_3$-N(CH$_3$)$_2$ | yellow |
| 16 | —C— | 4 | pyridinone with CH$_3$, CH$_3$, N-methylimidazolium, OH, =O, N-(CH$_2$)$_3$-N(CH$_3$)$_2$, Cl$^-$ | yellow |

TABLE 2-continued
EXAMPLES 9-34
| Ex. | B | n" | CC | Shade |
|---|---|---|---|---|
| 17 |  | 4 | 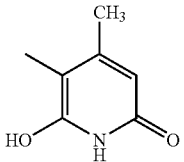 | yellow |
| 18 |  | 4 | 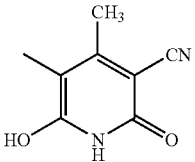 | yellow |
| 19 |  | 4 | 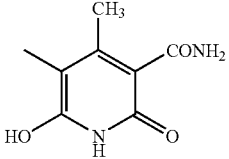 | yellow |
| 20 |  | 4 | 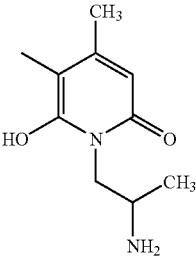 | yellow |
| 21 |  | 4 | 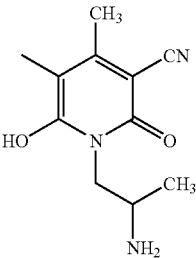 | yellow |

TABLE 2-continued
EXAMPLES 9-34
| Ex. | B | n" | CC | Shade |
|---|---|---|---|---|
| 22 |  | 4 | 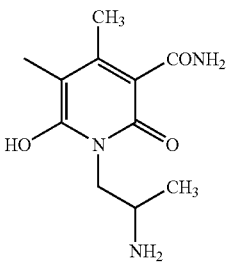 | yellow |
| 23 |  | 4 | 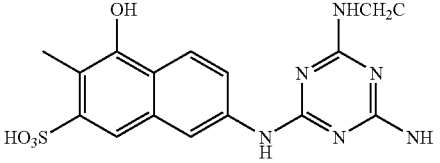 | orange |
| 24 | (—CH$_2$—O—CH$_2$)$_4$C | 4 | 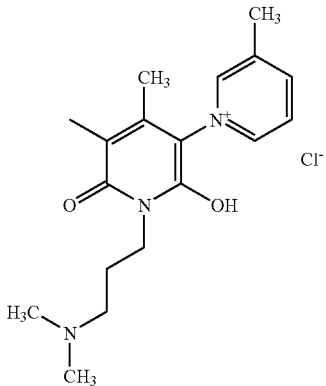 | yellow |
| 25 | (—CH$_2$—O—CH$_2$)$_4$C | 4 | 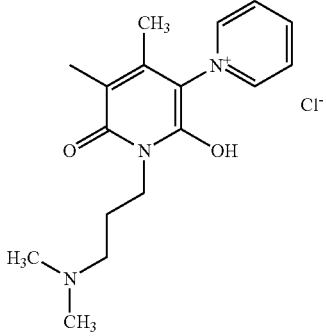 | yellow |

TABLE 2-continued
EXAMPLES 9-34
| Ex. | B | n" | CC | Shade |
|-----|---|----|----|-------|
| 26 | (—CH₂—O—CH₂—)₄C | 4 | 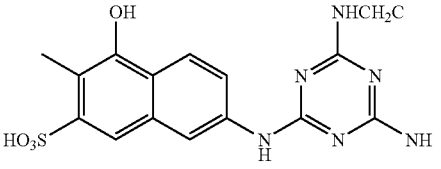 | orange |
| 27 | (—CH₂—O—CH₂CH₂—O—CH₂CH₂—O—CH₂—)₄C | 4 | 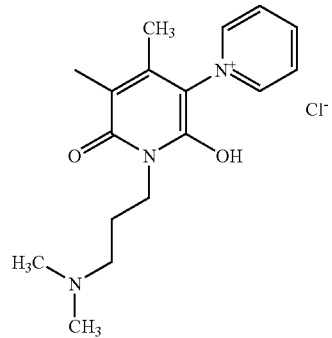 | yellow |
| 28 | (—CH₂—O—CH₂CH₂—O—CH₂CH₂—O—CH₂—)₄C | 4 | 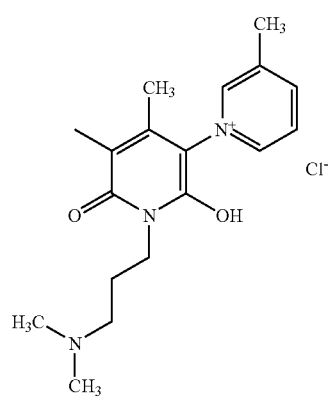 | yellow |
| 29 | (—CH₂—O—CH₂CH₂—O—CH₂CH₂—O—CH₂—)₄C | 4 | 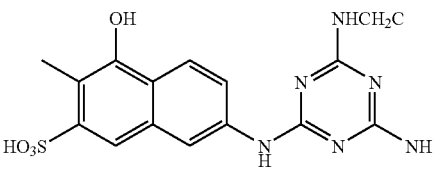 | orange |
| 30 | (—CH₂CH₂—O—CH₂—)₄C | 4 | 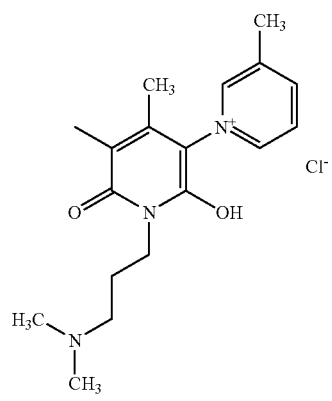 | yellow |

TABLE 2-continued

EXAMPLES 9-34

| Ex. | B | n" | CC | Shade |
|---|---|---|---|---|
| 31 | (—CH₂CH₂—O—CH₂)₄C | 4 | 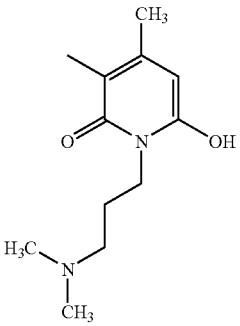 | yellow |
| 32 | (—CH₂CH₂—O—CH₂)₄C | 4 | 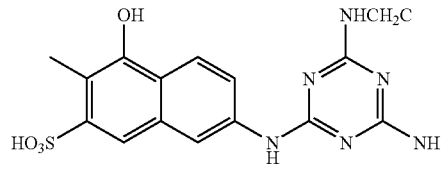 | orange |
| 33 | (—CH₂)₂NCH₂CH₂N(CH₂—)₂ | 4 | 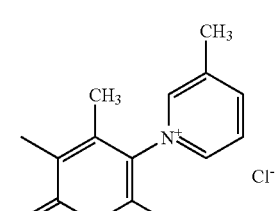 | yellow |
| 34 | (—CH₂)₂NCH₂CH₂N(CH₂—)₂ | 4 | 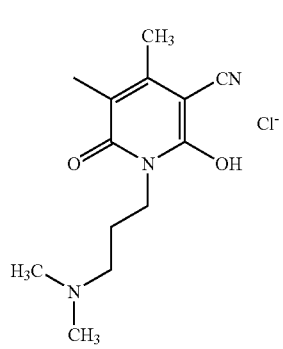 | yellow |

EXAMPLE 35

To a mixture of 200 parts of ice, 90 parts of 30% HCl, 80 parts of acetic acid and 30 parts of N,N-dimethyl-acetamide 50 parts of the amino compounds of Example 2 are added and diazotised with 21 parts of 4N solution of sodium nitrite. The temperature is maintained at 0° C.-5° C. by the addition of 100 parts of ice. To the diazo solution 378 parts of an approx. 20% aqueous solution of 6-hydroxy4-methyl-pyridonyl-(3)-3'-methylpyridinium chloride are added. By the addition of 15 parts of 30% solution of sodium hydroxide the pH value is adjusted to 3 at a temperature of 10° C.-20° C. After 1 hour stirring the pH value is adjusted to 10 with 30% solution of sodium hydroxide and the precipitated dyestuff is filtered off, washed with 10% solution of sodium carbonate and dried at 60° C. in vacuum to obtain a yellow powder which is a mixture containing compounds having the formula (VIIIa, VIIIb, VIIIc, VIIId)

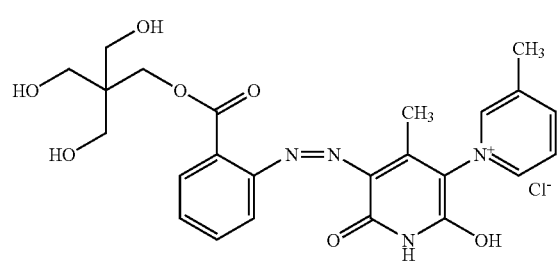
(VIIIa)
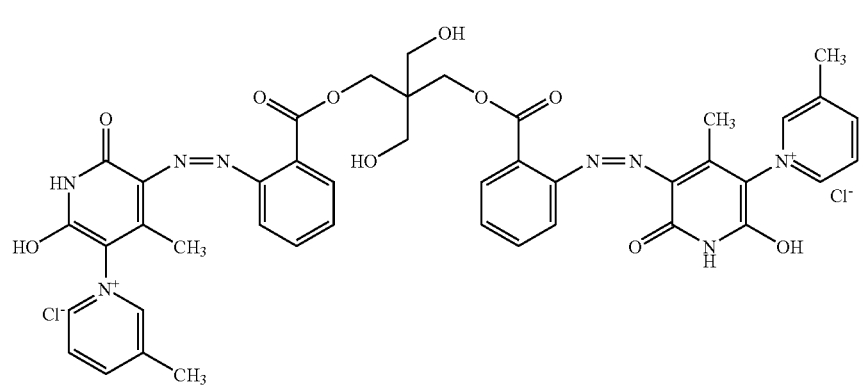
(VIIIb)
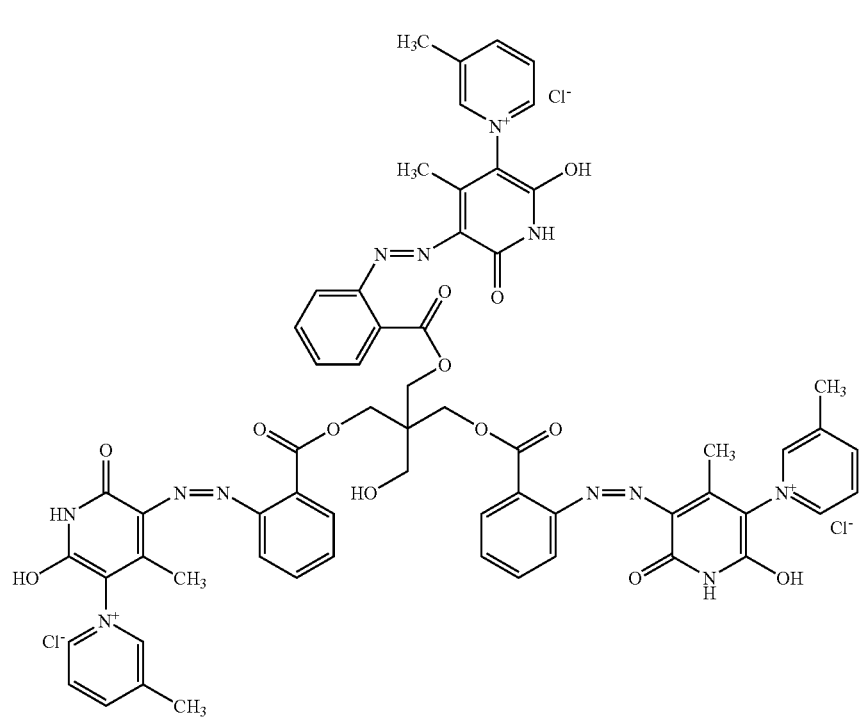
(VIIIc)

-continued (VIIId)

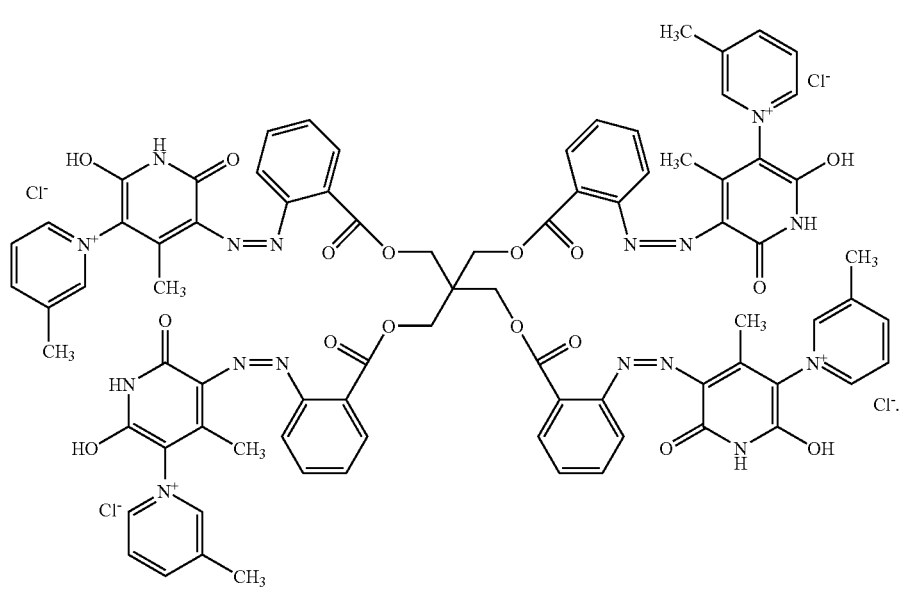

The mixture of these dyestuffs is very soluble in diluted acids, particularly organic acids such as formic acid, lactic acid, acetic acid and methoxyacetic acid. The solution dyes paper in brilliant yellow shade. The obtained dyeing shows excellent wet fastness (against water, alcohol, milk, soapy water, sodium chloride solution, urine, etc.).

Further mixtures of dyestuffs of the general formulae (IXa), (IXb), (IXc) and (IXd) may be produced analogously to the procedure given in Example 35.

(IXa)

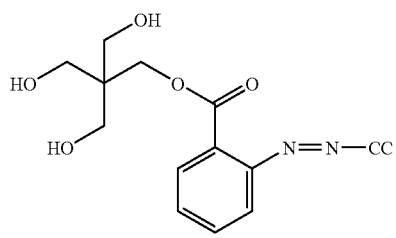

(IXc)

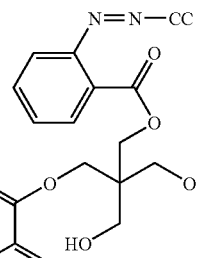
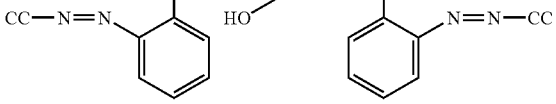

(IXb)

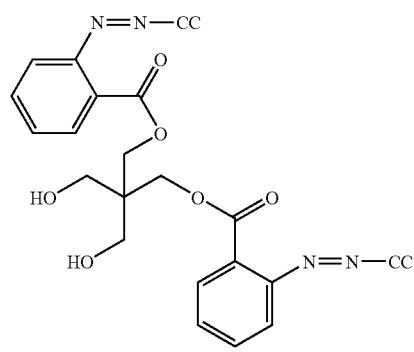

(IXd)

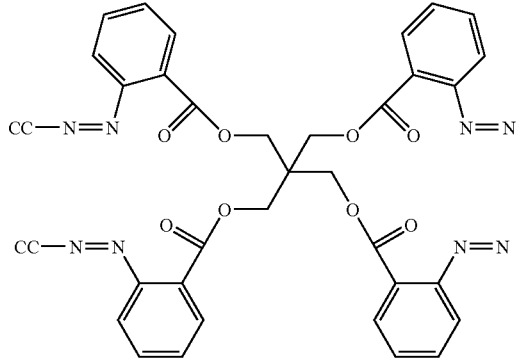

TABLE 3

EXAMPLES 36-54

| Ex. | CC | Shade |
|---|---|---|
| 36 | (structure: 4,5-dimethyl-6-hydroxy-1-[3-(methylamino)propyl]pyridin-2(1H)-one) | yellow |
| 37 | (structure: 3-cyano-4,5-dimethyl-6-hydroxy-1-[3-(methylamino)propyl]pyridin-2(1H)-one) | yellow |
| 38 | (structure: 3-carbamoyl-4,5-dimethyl-6-hydroxy-1-[3-(methylamino)propyl]pyridin-2(1H)-one) | yellow |
| 39 | (structure: 1-(4,5-dimethyl-6-hydroxy-2-oxo-1,2-dihydropyridin-3-yl)pyridinium chloride) | yellow |
| 40 | (structure: 1-{1-[3-(dimethylamino)propyl]-4,5-dimethyl-6-hydroxy-2-oxo-1,2-dihydropyridin-3-yl}pyridinium chloride) | yellow |

TABLE 3-continued
EXAMPLES 36-54
| Ex. | CC | Shade |
|---|---|---|
| 41 | 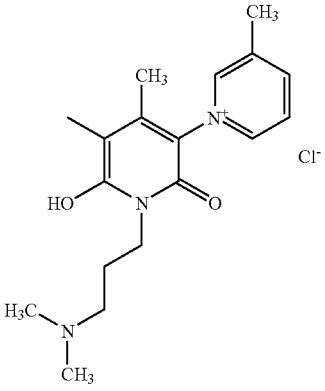 | yellow |
| 42 | 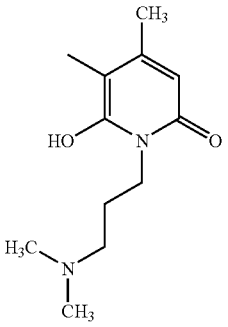 | yellow |
| 43 | 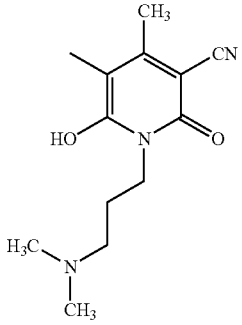 | yellow |
| 44 | 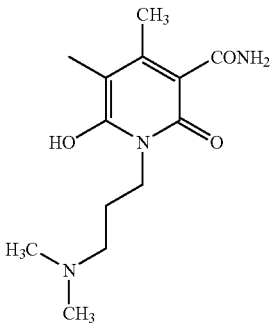 | yellow |

TABLE 3-continued

EXAMPLES 36-54

| Ex. | CC | Shade |
|---|---|---|
| 45 | 3-(3-methylimidazolium)-1-(3-dimethylaminopropyl)-4,5-dimethyl-6-hydroxy-2-oxo-pyridine chloride | yellow |
| 46 | 4,5-dimethyl-6-hydroxy-2-oxo-pyridine | yellow |
| 47 | 3-cyano-4,5-dimethyl-6-hydroxy-2-oxo-pyridine | yellow |
| 48 | 3-carboxamido-4,5-dimethyl-6-hydroxy-2-oxo-pyridine | yellow |
| 49 | 1-(2-aminopropyl)-4,5-dimethyl-6-hydroxy-2-oxo-pyridine | yellow |
| 50 | 1-(2-aminopropyl)-3-cyano-4,5-dimethyl-6-hydroxy-2-oxo-pyridine | yellow |

TABLE 3-continued

EXAMPLES 36-54

| Ex. | CC | Shade |
|---|---|---|
| 51 | (structure: pyridone with CH3, CONH2, HO, N-CH2-CH(CH3)-NH2) | yellow |
| 52 | (structure: naphthol-sulfonic acid linked via NH to triazine with two NH-CH(CH3)-CH2-NH2 substituents) | orange |
| 53 | (structure: naphthol-sulfonic acid linked via NH to triazine with two NH-CH2CH2CH2-N(CH2CH3)2 substituents) | orange |
| 54 | (structure: naphthol-sulfonic acid linked via NH to triazine with two NH-CH2CH2-OH substituents) | orange |

EXAMPLE 55

12.5 parts of Exp. 35 and 87.5 parts of C.I. Basic Brown 23 are mixed. This dye composition is useful to add to ground cellulose and will give paper made thereof a brown hue.

The parts relates to the total amount of dyestuff, which is 100. Furthermore additional auxiliaries may be added to this dye composition e.g. buffers, viscosity improvers, surface tension improvers, biocides, light stabilizers, UV absorbers, optical brighteners and ionic or nonionic surfactants.

Further mixtures of dyestuffs may be produced analogously to the procedure given in Example 55.

TABLE 4

EXAMPLES 56-66

| Exp | Component one | Component two | Wt-% of Dye I | Wt-% of Dye II |
|---|---|---|---|---|
| 56 | Exp. 26 | C.I. Basic Brown 23 | 27.5 | 72.5 |
| 59 | Exp. 28 | C.I. Basic Red 12 | 40 | 60 |
| 60 | Exp. 34 | C.I. Basic Blue 1 | 37.5 | 62.5 |
| 61 | Exp. 35 | C.I. Basic Brown 23 | 22.5 | 77.5 |
| 62 | Exp. 35 | C.I. Basic Red 14 | 97.5 | 2.5 |
| 63 | Exp. 35 | C.I. Basic Violet 10 | 90 | 10 |
| 64 | Exp. 35 | C.l. Basic Red 12 | 80 | 20 |
| 65 | Exp. 35 | C.I. Basic Blue 26 | 22.5 | 77.5 |
| 66 | Exp. 35 | C.I. Basic Blue 1 | 95 | 5 |
| 67 | Exp. 39 | C.I. Basic Red 12 | 50 | 50 |

The use examples, which follow, serve to illustrate the invention. In the examples, parts are weight percent, unless otherwise stated; the temperatures are reported in degrees Celsius.

USE EXAMPLE A

A hollander is used to grind 70 parts of chemically bleached sulfite softwood cellulose and 30 parts of chemically bleached sulfite birchwood cellulose into 2000 parts of water. 0.2 part of the dye from Example 8 is sprinkled in. After a mixing time of 20 minutes paper is made from the stuff. The thusly obtained absorbent paper has a yellow color. The wastewater is colorless.

USE EXAMPLE B 0.5 part of the dye solution of Example 35 is poured into 100 parts of bleached sulfite cellulose ground with 2000 parts of water in a hollander. Mixing for 15 minutes was followed by sizing. Paper made from this material has a yellow hue.

USE EXAMPLE C

An absorbent web of unsized paper is pulled at 40° C.-50° C. through a dye solution of the following composition:
0.5 part of the dye of Example 8,
0.5 part of starch and
99.0 parts of water Excess dye solution is squeezed off by two rolls. The dry paper web has a yellow color.

The method of Use Examples A to C is also suitable for dyeing with the dyes of tables 2 and 3.

USE EXAMPLE D 15 kg of wastepaper (woody), 25 kg of bleached groundwood and 10 kg of unbleached sulfate pulp were beaten in a pulper to form a 3% aqueous pulp suspension. The pulp suspension was diluted to 2% in a dyeing vat. This suspension was then admixed in succession with 5% of kaolin and 1.25 kg of a 5% acetic acid solution of the dye of Example 8, reckoned on dry total fiber, by stirring. After 20 minutes the pulp in the mixing vat is admixed with 1% (based on absolutely dry fiber) of a resin size dispersion. The homogeneous pulp suspension was adjusted with alum to pH 5 on the paper machine just upstream of the headbox.

The paper machine was used to produce 80 g/m² of yellow bag paper with a machine finish.

USE EXAMPLE E

A dry stock consisting of 60% groundwood and 40% unbleached sulfite pulp is beaten with sufficient water and ground to 40 SR freeness in a hollander for the dry content to be just above 2.5% and then adjusted with water to a dry content of exactly 2.5% for the high-density pulp.

200 parts of this high-density pulp are admixed with 5 parts of a 0.25% aqueous solution of the dye of Example 8, stirred for about 5 min., admixed with 2% of resin size and 4% of alum, based on dry stock, and again stirred for some minutes until homogeneous. The material is diluted with 500 parts of water to 700 parts by volume and used in a known manner to prepare sheets of paper by drainage on a sheet-former. These sheets of paper have a deep yellow color.

The method of Use Examples D and E is also suitable for dyeing with the dyes of tables 2 and 3.

USE EXAMPLE F 15 kg of wastepaper (woody), 25 kg of bleached groundwood and 10 kg of unbleached sulfate pulp were beaten in a pulper to form a 3% aqueous pulp suspension. The pulp suspension was diluted to 2% in a dyeing vat. This suspension was then admixed in succession with 5% of kaolin and 1.25 kg of a 5% acetic acid solution of the dye composition of Example 59, reckoned on dry total fiber, by stirring. After 20 minutes the pulp in the mixing vat is admixed with 1% (based on absolutely dry fiber) of a resin size dispersion. The homogeneous pulp suspension was adjusted with alum to pH 5 on the paper machine just upstream of the headbox.

The paper machine was used to produce 80 g/m² of brown bag paper with a machine finish.

USE EXAMPLE G

A ink composition for ink jet printing consists of
6 parts of a dye of the Example 22,
20 parts of glycerol and
74 parts of water.

This ink composition is used for printing papers, papery substrates, textile fiber materials and plastic films and plastic transparencies.

The invention claimed is:
1. A compound of formula (I)

$$\left[ \underset{O}{\underset{\|}{\overset{NH_2}{\text{Ar}}-C-A-CH_2}} \right]_{n'} - \underset{(CH_2OH)_m}{B} - \left[ CH_2-A-\underset{O}{\overset{\|}{C}}-\text{Ar}-N=N-CC \right]_{n''} \quad (I)$$

wherein
each A is independently —NH— or —O—,
B is
—[—(CH$_2$)$_{1-4}$—O—(CH$_2$)$_{1-4}$]$_4$C or
[—(CH$_2$)$_{1-3}$—O—(CH$_2$)$_{1-3}$—O—(CH$_2$)$_{1-3}$]$_4$C or
[—(CH$_2$)$_{1-2}$—O—(CH$_2$)$_{1-2}$—O—(CH$_2$)$_{1-2}$—O—(CH$_2$)$_{1-2}$]$_4$C or
[(—CH$_2$)$_{1-4}$]$_2$N(CH$_2$)$_{1-4}$N[(—CH$_2$)$_{1-4}$]$_2$
n' and n" are natural numbers and the sum of n' and n" is ≧2,
m is a natural number ≧0,
CC is a moiety of formula (a)

$$\text{(a)}$$

(structure: naphthol with OH, SO$_3$H, CH$_3$ substituents, linked via —N(R$_1$)—Y—phenyl—N(R$_1$)— bridge (repeated o times) to a triazine bearing $X_1$ and $X_2$)

wherein
$R_1$ is H; $C_{1-4}$alkyl; $C_{1-4}$alkyl monosubstituted by hydroxy, halogen, cyano or $C_{1-4}$alkoxy,
$X_1$ and $X_2$ independently of each other are halogen; an aliphatic, cycloahphatic, aromatic or heterocyclic amino group, said amino group comprising a protonatable nitrogen atom or a quaternary ammonium group, and being an aliphatic, cycloaliphatic, aromatic or heterocyclic mono($C_{1-4}$alkyl)-amino group, the $C_{1-4}$alkyl-group being unsubstituted or monosubstituted by halogen, $C_{1-4}$alkoxy, $C_{1-4}$alkyl, phenyl or hydroxy; an aliphatic, cycloaliphatic, aromatic or heterocyclic di($C_{1-4}$alkyl)-amino group, the $C_{1-4}$alkyl-groups being independently unsubstituted or monosubstituted by halogen, $C_{1-4}$alkyl, $C_{1-4}$alkoxy, phenyl or hydroxy; a $C_{5-6}$cycloalkylamino group, the cycloalkyl group being unsubstituted or substituted by one or two $C_{1-2}$alkyl groups; a phenylamino group, the phenyl ring being unsubstituted or substituted by one or two groups selected from halogen, $C_{1-4}$alkyl, $C_{1-4}$alkoxy, hydroxy and phenoxy; or a 5- or 6-membered ring containing one or two hetero atoms, in addition to N, O or S, which heterocyclic ring is unsubstituted or substituted by one or two $C_{1-4}$alkyl groups; or a group Z, where Z is independently selected from the group consisting of:

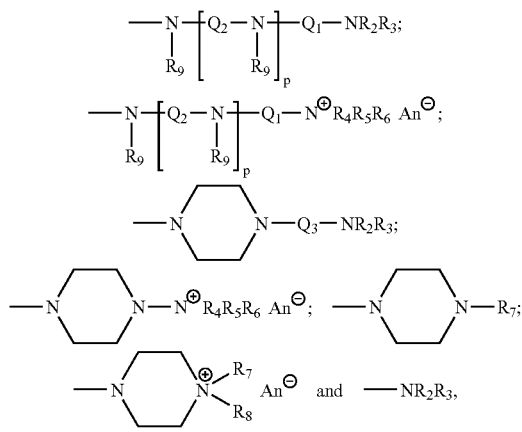

wherein
  p is 0 or an integer 1, 2 or 3,
  each $R_9$ is independently hydrogen; unsubstituted $C_{1-4}$alkyl or $C_{1-4}$alkyl monosubstituted by hydroxy, halogen, cyano or $C_{1-4}$alkoxy,
  each $R_2$ and $R_3$ is independently hydrogen; unsubstituted $C_{1-6}$alkyl; $C_{2-6}$alkyl monosubstituted by hydroxy, amino or cyano; phenyl or phenyl-$C_{1-4}$alkyl, where the phenyl ring of the latter two groups is unsubstituted or substituted by one to three groups selected from chlorine, $C_{1-4}$alkyl, $C_{1-4}$alkoxy, unsubstituted $C_{5-6}$cycloalkyl or $C_{5-6}$cycloalkyl substituted by one to three $C_{1-4}$alkyd groups or a pyridinium ring, or
  $R_2$ and $R_3$ together with the nitrogen atom to which they are attached, form a 5- or 6-membered ring containing one to three hetero atoms (in addition to N, one or two further N, O or S), which heterocyclic ring is unsubstituted or substituted by one or two $C_{1-4}$alkyl groups,
  each $R_4$ and $R_5$ has independently one of significances of $R_2$ and $R_3$, except hydrogen,
  $R_6$ is $C_{1-4}$alkyd or benzyl with the exception that $R_6$ is not benzyl when $R_4$ and $R_5$ have one of the cyclic significations of $R_2$ and $R_3$, or
  $R_4$, $R_5$ and $R_6$ together with the nitrogen atom to which they are attached, form a pyridinium ring which is unsubstituted or substituted by one or two methyl groups,
  $Q_1$ is $C_{2-8}$alkylene; $C_{3-6}$alkylene substituted by one or two hydroxy groups; $C_{1-6}$alkylene-1,3- or 1,4-phenylene, or —*NHCOCH$_2$—, where * denotes the atom bound to —NR$_9$,
  $Q_2$ is $C_{2-8}$alkylene; $C_{3-6}$alkylene substituted by one or two hydroxy groups; $C_{1-6}$alkylene-1,3- or -1,4-phenylene or 1,3- or 1,4-phenylene,
  $Q_3$ is $C_{2-8}$alkylene,
  $R_7$ is hydrogen; unsubstituted $C_{1-6}$alkyl or $C_{1-6}$alkyl monosubstituted by hydroxy, cyano, chlorine or phenyl,
  $R_8$ is unsubstituted $C_{1-6}$alkyl or $C_{1-6}$alkyl monosubstituted by hydroxy, cyano or chlorine, and An$^\ominus$ is a non-chromophoric anion,
  Y is direct bond, —CO— or —CO—NH—*, wherein the asterisk signifies the bond to the benzene ring and
  o is 0 or 1 or
CC is a moiety of formula (b)

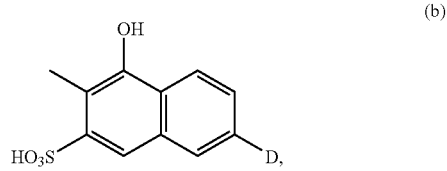

wherein
  D is a basic group —NR$_1$-Q$_4$-NR$_2$R$_3$ or a cationic group —NR$_1$-Q$_4$-N$^+$R$_4$R$_5$R$_6$, in which R$_1$, R$_2$, R$_3$, R$_4$, R$_5$ and R$_6$ have the same meanings as above and
  $Q_4$ is $C_{2-6}$alkylene, which may be interrupted by —O—, —S— or —N(R$_1$)—; $C_{2-3}$alkylene substituted by one or two hydroxy groups; or —*NHCOCH$_2$—, where * denotes the atom bound to the —NR$_1$-radical,
or CC is a moiety of formula (c$_1$) or (c$_2$)

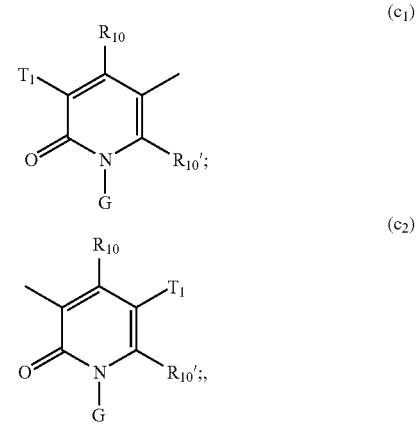

wherein
  each $R_{10}$ independently of each other is H; $C_{1-4}$alkyl; $C_{5-6}$cycloalkyl; phenyl, benzyl or phenylethyl,
  each $R_{10}'$ independently of each other is H; —OH or $C_{1-4}$alkyl
  each $T_1$ independently of each other is H; —CN; —COOR$_{15}$; CONR$_{16}$R$_{17}$; SO$_2$NR$_{16}$R$_{17}$;

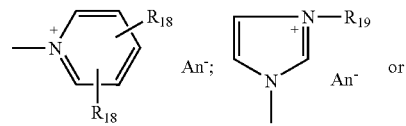

-continued

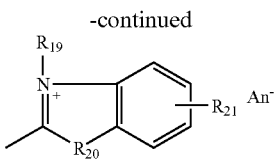

G is H; —R$_{11}$NHR$_{12}$ or —R$_{11}$NR$_{13}$R$_{14}$, wherein
R$_{11}$ is C$_{1-6}$alkylene or C$_{2-6}$alkenylene,
R$_{12}$ and R$_{13}$ independently of each other are H; unsubstituted C$_{1-6}$alkyl; C$_{2-6}$alkyl substituted by OH, CN or halogen; phenyl-C$_{1-3}$ alkyl, wherein the phenyl radical is optionally substituted from 1 to 3 times, by a substituent selected from the group consisting of: chlorine, C$_{1-4}$alkyl or C$_{1-4}$alkoxy; unsubstituted C$_{5-6}$cycloalkyl and C$_{5-6}$cycloalkyl substituted from 1 to 3 times by C$_{1-4}$alkyl groups,
R$_{14}$ is any of the meanings of R$_{12}$ or R$_{13}$ or hydrogen,
R$_{15}$ is a C$_{1-6}$alkyl radical or phenyl-C$_{1-3}$alkyl radical,
R$_{16}$ and R$_{17}$ independently of each other are H or a C$_{1-4}$alkyl radical,
R$_{18}$ independently of each other signifies H; a C$_{1-4}$alkyl radical; —NR$_{16}$R$_{17}$—(CH$_2$)$_{2-4}$—NR$_{16}$R$_{17}$ or —CONR$_{16}$R$_{17}$,
R$_{19}$ is a C$_{1-4}$alkyl radical or a hydroxy-C$_{1-4}$alkyl radical,
R$_{20}$ is —S— or —O—,
R$_{21}$ is hydrogen or a C$_{1-4}$alkyl radical and
An$^-$ is a non-chromophoric anion,
with the provisos that
(i) the sum of n', n" and m is smaller as or equal to the valencies of B,
(ii) when the sum of n' and n"=2 then m is ≧1,
(iii) when the sum of n' and n"=3 and A=NH then m is ≧1
and their salts and mixtures thereof.

2. A compound according to claim 1 where A is —O—.

3. A compound according to claim 1 wherein CC is formulae (c$_2$) or (a$_1$):

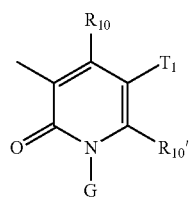 (c$_2$)

where
R$_{10}$ is H; —CH$_3$ or —CH$_2$CH$_3$,
T$_1$ is H; —CN; —CONH$_2$; —CONHCH$_3$;

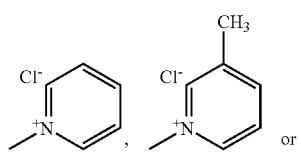

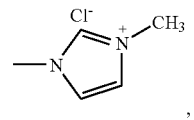

R$_{10}$' is H; —CH$_3$ or —OH,
G is H or —(CH$_2$)$_{2-4}$NR$_{13}$R$_{14}$,
where R$_{13}$ and R$_{14}$ are independently from each other H; —CH$_3$ or —CH$_2$CH$_3$,
or

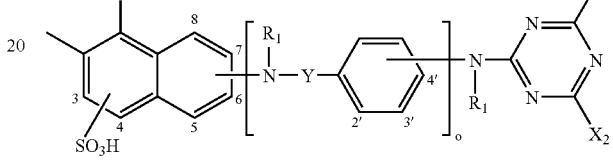 (a$_1$)

where
each R$_1$ is independently from each other H; —CH$_3$, —CH$_2$CH$_3$ or substituted C$_{1-4}$alkyl,
X$_1$ and X$_2$ are independently from each other halogen or —NR$_2$R$_3$ wherein R$_2$ and R$_3$ are independently from each other H; C$_{1-4}$alkyl; —C$_{2-4}$alkylene-NH$_2$— or —C$_{2-4}$alkylene-OH—;
Y signifies a direct bond;

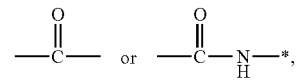

wherein the asterisk is the bond to the benzene ring and
o is 0 or 1.

4. Mixtures of compounds comprising at least one compound of formula (I) according to claim 1.

5. Mixtures according to claim 4 comprising at least one compound according to formula (I) and at least one compound selected from the group consisting of:

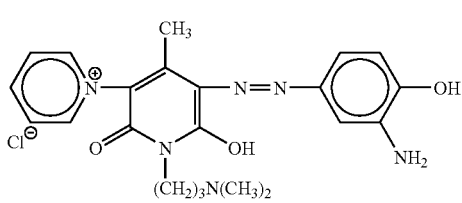 1a

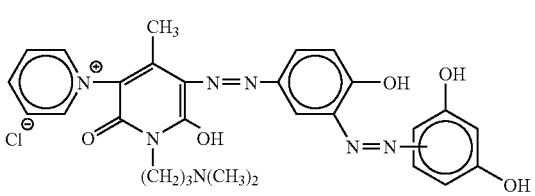 1b

-continued

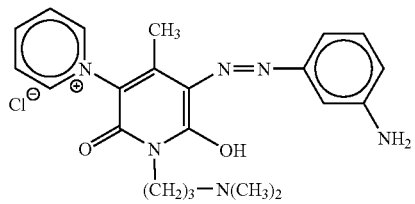
2c

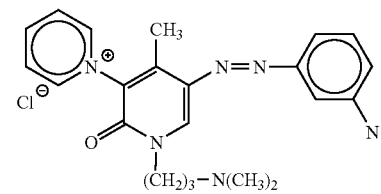
2d

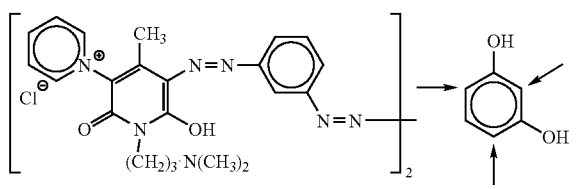
2e

-continued

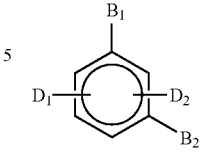
5 wherein D1 is a radical and $B_1$, $B_2$, $D_2$, $R_1$, $R_2$, $R_t$ and M are indicated in Table I below;

TABLE I

| Ex. | $R_1$ | M | $R_2$ | $R_t$ (position on ring B) | Position of the azo ① on ring B | $B_1$ | $B_2$ | $D_2$ |
|---|---|---|---|---|---|---|---|---|
| 3 | —⊕N⃝ A⊖ | | H | H | 4 | OH | OH | H |
| 4 | " | " | H | H | 4 | OH | OH | $D_1$ |
| 5 | " | " | H | H | 4 | $NH_2$ | $NH_2$ | H |
| 6 | " | " | H | H | 4 | $NH_2$ | $NH_2$ | $D_1$ |
| 7 | " | " | H | H | 4 | $NH_2$ | OH | H |
| 8 | " | | H | H | 3 | OH | OH | 4 |
| 9 | " | | H | H | 3 | OH | OH | $D_1$ |
| 10 | " | | H | H | 3 | $NH_2$ | $NH_2$ | H |
| 11 | " | | H | H | 3 | $NH_2$ | $D_1$ | |
| 12 | " | | H | H | 3 | OH | $NH_2$ | H |
| 13 | " | | H | H | 4 | OH | OH | H |
| 14 | " | | H | H | 4 | OH | OH | $D_1$ |
| 15 | " | | H | H | 4 | OH | $NH_2$ | H |
| 16 | —⊕N⃝-CH₃ A⊖ | | H | H | 3 | OH | OH | H |
| 17 | " | | H | H | 3 | OH | OH | $D_1$ |
| 18 | " | | H | H | 4 | $NH_2$ | $NH_2$ | H |
| 19 | " | | H | H | 4 | $NH_2$ | $NH_2$ | $D_1$ |
| 20 | " | | H | H | 4 | $NH_2$ | OH | H |
| 21 | —N⃝ A⊖ | —$(CH_2)_3$—$N(C_2H_5)_2$ | H | H | 3 | OH | OH | H |

TABLE I-continued

| Ex. | R₁ | M | R₂ | R_t (position on ring B) | Position of the azo ① on ring B | B₁ | B₂ | D₂ |
|---|---|---|---|---|---|---|---|---|
| 22 | " | " | H | H | 3 | OH | OH | D₁ |
| 23 | " | " | H | H | 4 | NH₂ | NH₂ | H |
| 24 | " | " | H | H | 4 | NH₂ | OH | H |
| 25 | " | " | H | H | 4 | OH | OH | H |
| 26 | —CN | " | H | H | 3 | OH | OH | H |
| 27 | " | " | H | H | 3 | OH | OH | D₁ |
| 28 | " | " | H | H | 4 | OH | OH | H |
| 29 | " | " | H | H | 4 | OH | NH₂ | H |
| 30 | " | " | H | H | 4 | NH₂ | NH₂ | H |
| 31 | —CONH₂ | " | H | H | 3 | OH | OH | H |
| 32 | " | " | H | H | 3 | OH | OH | D₁ |
| 33 | " | " | H | H | 4 | NH₂ | NH₂ | H |
| 34 | H | " | H | H | 3 | OH | OH | H |
| 35 | H | " | H | H | 3 | OH | OH | D₁ |
| 36 | H | " | H | H | 4 | NH₂ | NH₂ | H |
| 37 | H | " | H | H | 4 | NH₂ | NH₂ | H |
| 38 | —CN | —(CH₂)₃N(C₂H₅)₂ | H | H | 3 | OH | OH | H |
| 39 | —CONH₂ | " | H | H | 4 | OH | OH | H |
| 40 | H | " | H | H | 4 | NH₂ | NH₂ | H |
| 41 | [N-methylpyridinium A⁻] | —(CH₂)₃—N(CH₃)₂ | OH | H | 5 | OH | OH | H |
| 42 | " | H | OH | H | 5 | OH | OH | H |
| 43 | " | H | H | OH-(4) | 3 | OH | OH | H |
| 44 | H | —(CH₂)₃—N(CH₃)₂ | OH | H | 5 | OH | OH | H |
| 45 | H | " | H | OH-(4) | 3 | OH | OH | H |
| 46 | H | " | H | H | 4 | OH | OH | H |

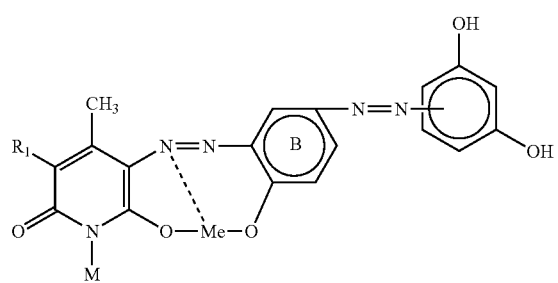

wherein R₁, M and Me are indicated in Table 2

TABLE 2

| Ex. | R₁ | M | Me Metal complex |
|---|---|---|---|
| 47 | [N-methylpyridinium A⁻] | —(CH₂)₃—N(CH₃)₂ | 1:1-Cu |
| 48 | " | " | 1:2-Cr |
| 49 | " | " | 1:2-Co |
| 50 | " | " | 1:2-Fe |
| 51 | " | H | 1:1-Cu |
| 52 | " | H | 1:2-Cr |
| 53 | " | H | 1:2-Co |
| 54 | " | H | 1:2-Fe |

TABLE 2-continued

| Ex. | R₁ | M | Me Metal complex |
|---|---|---|---|
| 55 | [3-methyl-N-methylpyridinium A⁻] | H | 1:1-Cu |
| 56 | " | H | 1:2-Fe |
| 57 | " | —(CH₂)₃N(CH₃)₂ | 1:1-Cu |
| 58 | " | " | 1:2-Cr |
| 59 | " | " | 1:2-Co |
| 60 | " | " | 1:2-Fe |

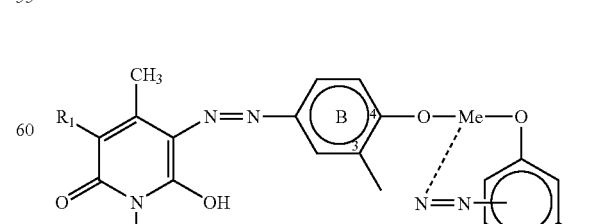

wherein R₁, M and Me are indicated in Table 3 below;

TABLE 3
| Ex. | R₁ | M | Me Metal complex |
|---|---|---|---|
| 61 | (N-methylpyridinium A⁻) | H | 1:1-Cu |
| 62 | " | H | 1:2-Cr |
| 63 | " | H | 1:2-Co |
| 64 | " | H | 1:2-Fe |
TABLE 3-continued
| Ex. | R₁ | M | Me Metal complex |
|---|---|---|---|
| 65 | (3-methyl-N-methylpyridinium A⁻) | H | 1:1-Cu |
| 66 | " | H | 1:2-Fe |
| 67 | H | —(CH₂)₃N(CH₃)₂ | 1:1-Cu |
| 68 | H | " | 1:2-Cr |
| 69 | H | " | 1:2-Co |
| 70 | H | " | 1:2-Fe |
Example 71
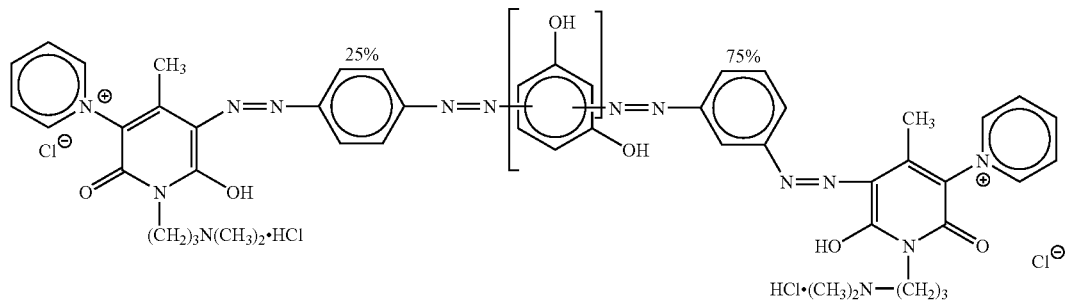
Example 72
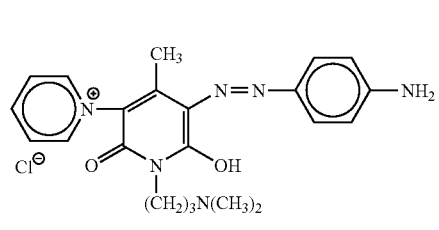
Example 72a
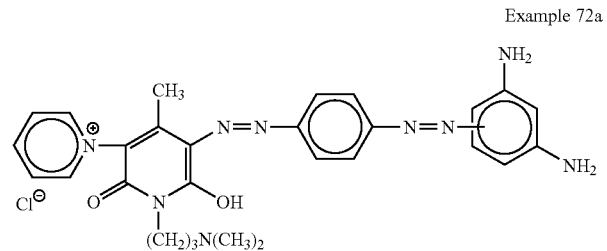
Example 72b
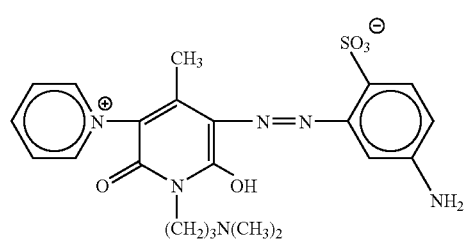

-continued
Example 72c
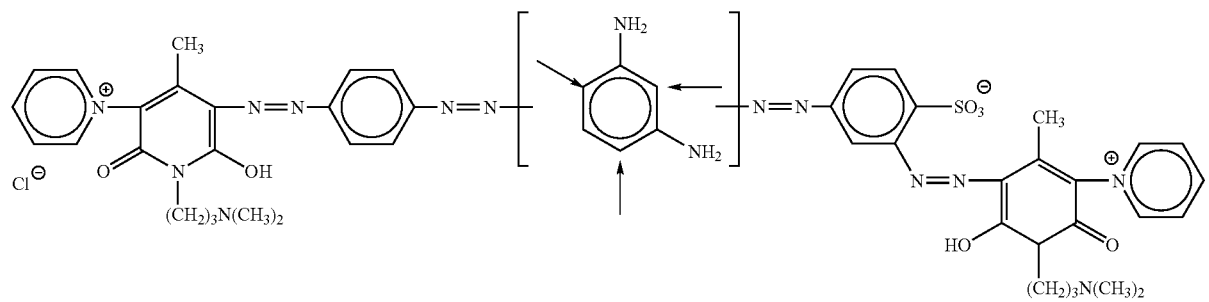
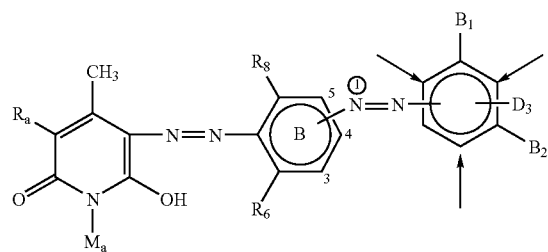
wherein $D_3$ is hydrogen or a radical of formula
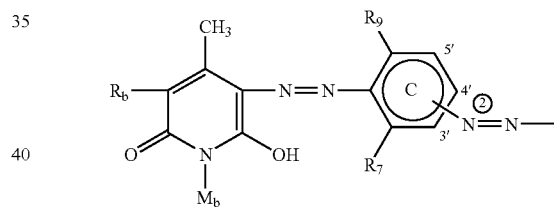
and $B_1$, $B_2$, $R_a$, $R_b$, $R_6$, $R_7$, $R_8$, $R_9$, $M_a$, and $M_b$ are as Indicated in Table 4;
TABLE IV
Significances of Ma and Mb
$M_1$ is H
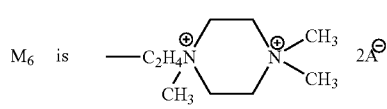
$M_2$ is —(CH$_2$)$_3$N(CH$_3$)$_2$
$M_3$ is —(CH$_2$)$_2$N(C$_2$H$_5$)$_2$
$M_7$ is —(CH$_2$)$_3$N$^{\oplus}$(CH$_3$)$_3$ A$^{\ominus}$
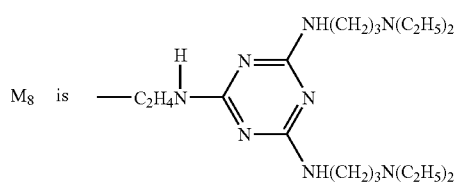

TABLE IV-continued

M₄ is —C₂H₄—N(piperazine)NH 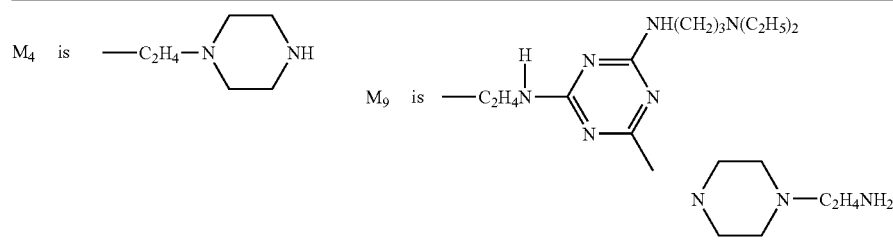

M₉ is —C₂H₄NH—(triazine with NH(CH₂)₃N(C₂H₅)₂ and piperazine-C₂H₄NH₂ substituents)

M₅ is —C₂H₄—N(piperazine)N—CH₃

M₁₀ is —(CH₂)₂NH₂

Significances of Ra and Rb

R₁ is H

R₂ is 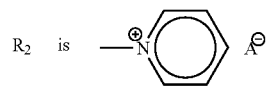 (pyridinium A⁻)

R₃ is 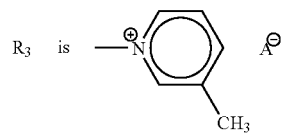 (methylpyridinium A⁻)

R₄ is CN

R₅ is 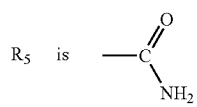 —C(=O)NH₂

| Ex. | Ra | Ma | R₆ | R₈ | Position of the azo ① on ring B | H or D₃ | Rb | Mb | R₇ | R₉ | Position of the azo ② on ring C | B₁ | B₂ |
|---|---|---|---|---|---|---|---|---|---|---|---|---|---|
| 73 | R₂ | M₂ | SO₃H | H | 3 | H | — | — | — | H | — | OH | OH |
| 74 | R₂ | M₂ | " | H | 4 | H | — | — | — | H | — | OH | NH₂ |
| 75 | R₂ | M₂ | " | H | 4 | H | — | — | — | H | — | NH₂ | NH₂ |
| 76 | R₂ | M₂ | " | H | 3 | D₃ | R₂ | M₂ | SO₃H | H | 3' | NH₂ | NH₂ |
| 77 | R₂ | M₂ | " | H | 3 | D₃ | R₂ | M₂ | H | H | 4' | NH₂ | NH₂ |
| 78 | R₂ | M₂ | " | H | 3 | D₃ | R₂ | M₂ | H | H | 4' | NH₂ | NH₂ |
| 79 | R₂ | M₂ | " | H | 3 | D₃ | R₂ | M₂ | H | H | 4' | NH₂ | OH |
| 80 | R₂ | M₂ | " | H | 3 | D₃ | R₂ | M₂ | H | H | 4' | OH | OH |
| 81 | R₂ | M₂ | " | H | 4 | D₃ | R₂ | M₂ | H | H | 3' | NH₂ | NH₂ |
| 82 | R₃ | M₁ | H | H | 3 | D₃ | R₂ | M₂ | SO₃H | H | 4' | NH₂ | NH₂ |
| 83 | R₁ | M₄ | H | H | 3 | D₃ | R₂ | M₅ | " | H | 4' | OH | NH₂ |
| 84 | R₄ | M₄ | H | H | 3 | D₃ | R₂ | M₆ | " | H | 4' | NH₂ | NH₂ |
| 85 | R₅ | M₄ | H | H | 3 | D₃ | R₂ | M₇ | " | H | 4' | NH₂ | NH₂ |
| 86 | R₂ | M₂ | SO₃H | H | 4 | D₃ | R₂ | M₂ | H | H | 3' | OH | NH₂ |
| 87 | R₂ | M₂ | " | H | 4 | D₃ | R₂ | M₂ | H | H | 3' | OH | OH |
| 88 | R₂ | M₈ | " | H | 4 | D₃ | R₂ | M₁ | H | H | 3' | OH | OH |
| 89 | R₂ | M₈ | " | H | 4 | D₃ | R₂ | M₂ | H | H | 3' | OH | NH₂ |
| 90 | R₂ | M₈ | H | H | 4 | D₃ | R₂ | M₄ | SO₃H | H | 3' | NH₂ | NH₂ |
| 91 | R₂ | M₉ | H | H | 4 | D₃ | R₂ | M₅ | SO₃H | H | 3' | OH | NH₂ |
| 92 | R₂ | M₉ | H | H | 3 | D₃ | R₄ | M₃ | " | H | 4' | OH | OH |
| 93 | R₂ | M₈ | H | H | 3 | D₃ | R₅ | M₄ | " | H | 4' | NH₂ | NH₂ |
| 94 | R₂ | M₃ | H | H | 4 | D₃ | R₂ | M₃ | " | H | 3' | NH₂ | NH₂ |
| 95 | R₂ | M₂ | H | CH₃ | 3 | D₃ | R₂ | M₂ | " | H | 4' | OH | OH |
| 96 | R₂ | M₃ | H | Cl | 3 | D₃ | R₂ | M₃ | " | H | 4' | NH₂ | NH₂ |
| 97 | R₂ | M₂ | H | OCH₃ | 3 | D₃ | R₂ | M₄ | " | H | 4' | NH₂ | NH₂ |
| 98 | R₂ | M₇ | SO₃H | H | 4 | D₃ | R₂ | M₇ | H | Cl | 3' | OH | OH |
| 99 | R₂ | M₈ | " | H | 4 | D₃ | R₂ | M₂ | H | CH₃ | 3' | OH | NH₂ |
| 100 | R₂ | M₆ | " | H | 4 | D₃ | R₂ | M₂ | H | OCH₃ | 3' | NH₂ | NH₂ |
| 101 | R₂ | M₂ | " | H | 3 | D₃ | R₂ | M₂ | H | H | 3' | OH | NH₂ |
| 102 | R₂ | M₂ | " | H | 4 | D₃ | R₂ | M₂ | H | H | 4' | NH₂ | NH₂ |
| 103 | R₂ | M₂ | " | H | 4 | D₃ | R₂ | M₂ | SO₃H | H | 4' | NH₂ | NH₂ |
| 104 | R₂ | M₂ | " | H | 3 | D₃ | R₂ | M₂ | H | H | 3' | NH₂ | NH₂ |
| 105 | R₂ | M₂ | " | H | 4 | D₃ | R₂ | M₂ | H | H | 4' | NH₂ | OH |
| 106 | R₂ | M₂ | " | H | 3 | D₃ | R₂ | M₂ | SO₃H | H | 4' | OH | NH₂ |
| 107 | R₂ | M₁₀ | " | H | 3 | D₃ | R₂ | M₂ | H | H | 3' | OH | OH |

Example 108a

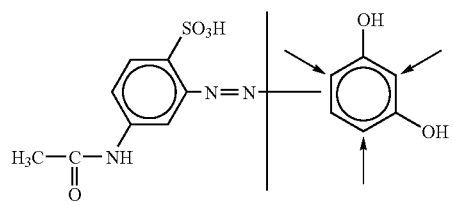

Example 108b

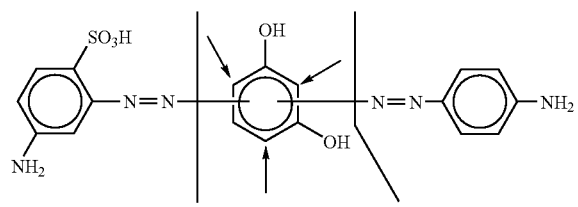

Example 108c

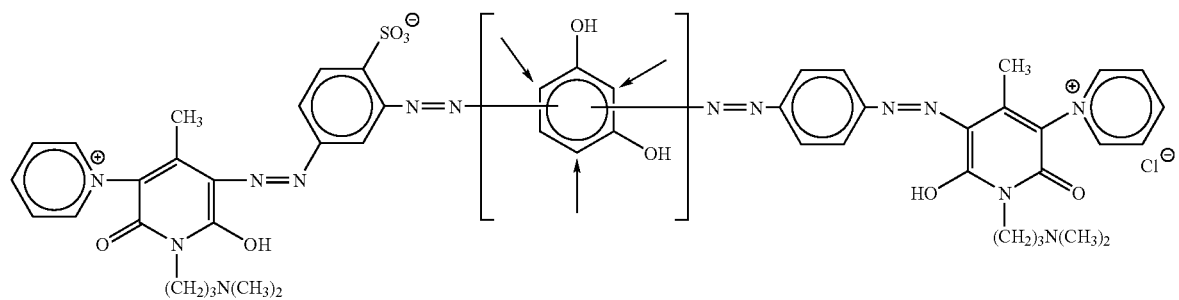

Example 108d

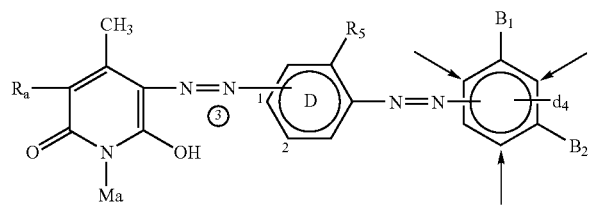

wherein d4 is H or D4

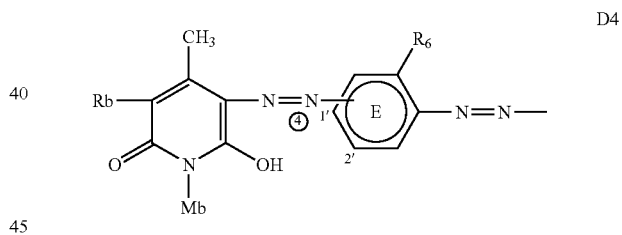

D4 and $R_a$, $R_b$, $R_5$, $R_6$, $B_1$, $B_2$, $M_a$, and $M_b$ are as indicated in Table 5 below;

TABLE V

| Ex. Nr. | Ra | Ma | $R_5$ | Position of the azo ③ on ring D | $d_4$ | $R_b$ | $M_b$ | $R_6$ | Position of the azo ④ on ring E | $B_1$ | $B_2$ |
|---|---|---|---|---|---|---|---|---|---|---|---|
| 109 | $R_2$ | $M_2$ | $SO_3H$ | 1 | H | — | — | — | — | OH | OH |
| 110 | $R_2$ | $M_2$ | " | 1 | H | — | — | — | — | $NH_2$ | $NH_2$ |
| 111 | $R_2$ | $M_2$ | " | 2 | H | — | — | — | — | OH | $NH_2$ |
| 112 | $R_2$ | $M_2$ | " | 2 | H | — | — | — | — | $NH_2$ | $NH_2$ |
| 113 | $R_2$ | $M_2$ | " | 1 | $D_4$ | $R_2$ | $M_2$ | H | 1' | OH | $NH_2$ |
| 114 | $R_2$ | $M_2$ | " | 1 | $D_4$ | $R_2$ | $M_2$ | H | 1' | $NH_2$ | $NH_2$ |
| 115 | $R_2$ | $M_2$ | " | 1 | $D_4$ | $R_2$ | $M_2$ | $SO_3H$ | 1' | OH | OH |
| 116 | $R_2$ | $M_2$ | " | 1 | $D_4$ | $R_2$ | $M_2$ | H | 2' | OH | OH |
| 117 | $R_2$ | $M_2$ | " | 1 | $D_4$ | $R_2$ | $M_2$ | H | 2' | $NH_2$ | $NH_2$ |
| 118 | $R_2$ | $M_2$ | " | 1 | $D_4$ | $R_2$ | $M_2$ | $SO_3H$ | 2' | OH | $NH_2$ |
| 119 | $R_2$ | $M_2$ | " | 2 | $D_4$ | $R_2$ | $M_2$ | " | 2' | OH | OH |
| 120 | $R_3$ | $M_3$ | " | 1 | $D_4$ | $R_3$ | $M_3$ | H | 1' | OH | OH |
| 121 | $R_2$ | $M_4$ | " | 1 | $D_4$ | $R_2$ | $M_4$ | H | 2' | $NH_2$ | $NH_2$ |
| 122 | $R_2$ | $M_5$ | H | 1 | $D_4$ | $R_2$ | $M_5$ | $SO_3H$ | 2' | $NH_2$ | OH |

TABLE V-continued
| Ex. Nr. | Ra | Ma | R5 | Position of the azo ③ on ring D | d4 | Rb | Mb | R6 | Position of the azo ④ on ring E | B1 | B2 |
|---|---|---|---|---|---|---|---|---|---|---|---|
| 123 | R2 | M5 | H | 2 | D4 | R2 | M6 | " | 1' | OH | OH |
| 124 | R3 | M7 | H | 2 | D4 | R3 | M7 | " | 1' | NH2 | OH |
| 125 | R1 | M8 | SO3H | 2 | D4 | R1 | M8 | " | 1' | OH | OH |
| 126 | R1 | M8 | " | 2 | D4 | R1 | M8 | H | 1' | NH2 | NH2 |
| 127 | R2 | M9 | " | 1 | D4 | R2 | M9 | H | 2' | OH | NH2 |
| 128 | R2 | M2 | " | 2 | D4 | R2 | M2 | H | 1' | OH | OH |
| 129 | R2 | M2 | H | 2 | D4 | R2 | M2 | SO3H | 1' | OH | OH |
| 130 | R2 | M2 | SO3H | 2 | D4 | R2 | M2 | H | 1' | NH2 | NH2 |
| 131 | R2 | M2 | H | 2 | D4 | R2 | M2 | SO3H | 1' | NH2 | NH2 |
| 132 | R2 | M2 | SO3H | 2 | D4 | R2 | M2 | " | 1' | NH2 | NH2 |
| 133 | R2 | M2 | " | 1 | D4 | R2 | M2 | " | 1' | NH2 | NH2 |
| 134 | R2 | M2 | H | 2 | D4 | R2 | M2 | " | 1' | OH | NH2 |
| 135 | R2 | M2 | SO3H | 2 | D4 | R2 | M2 | " | 1' | OH | NH2 |
| 136 | R2 | M2 | " | 1 | D4 | R2 | M2 | " | 1' | OH | NH2 |
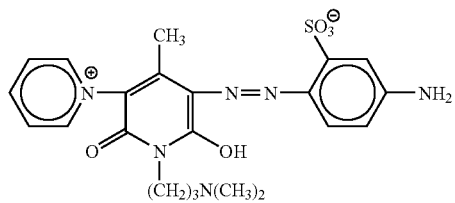
Example 137a
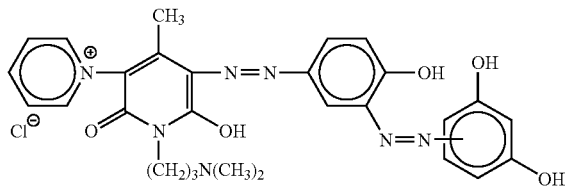
Example 137b
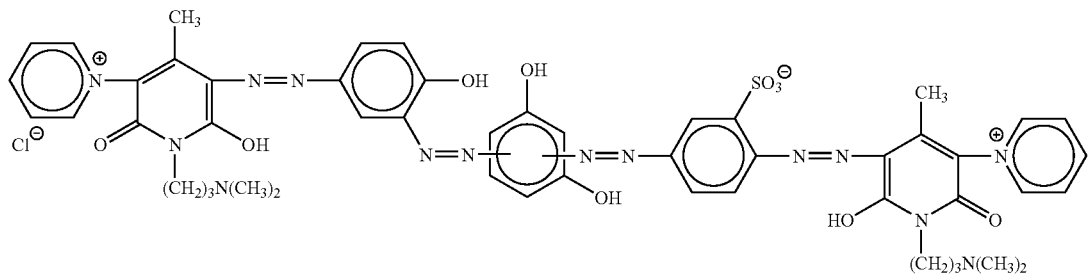
Example 137c
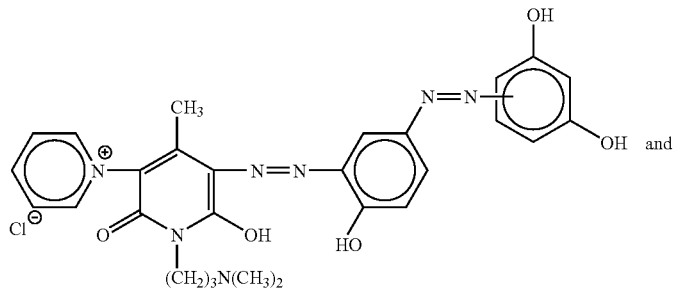
Example 137d -continued
Example 137e
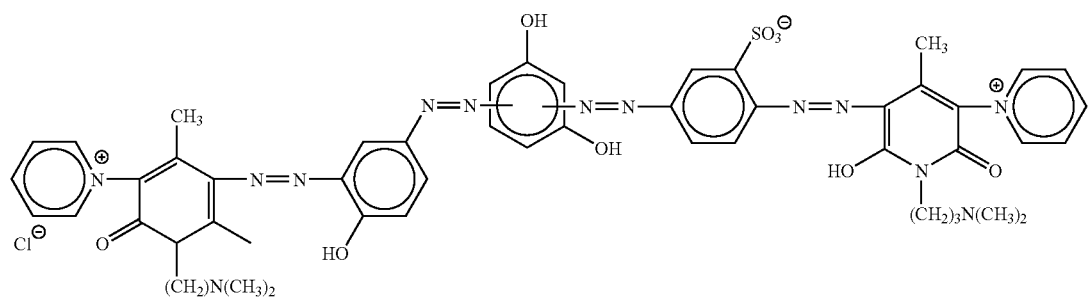
and a dye selected from the group consisting of: C.I. Basic Red; C.I. Basic Brown; C.I. Basic Blue; C.I. Basic Violet and combinations thereof.
6. Mixtures according claim 4 comprising from 2 to 98 parts (by weight) of at least one compound of formula (I) as component one and at least one compound selected from the group consisting of:
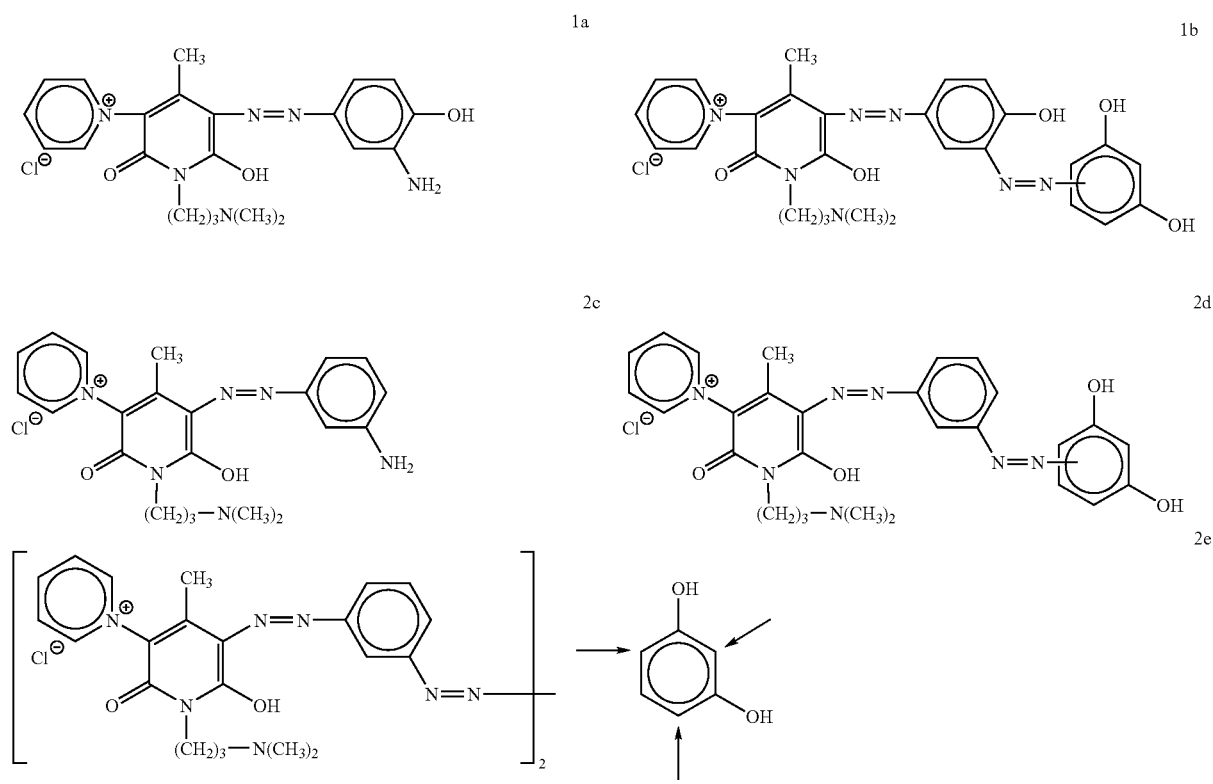
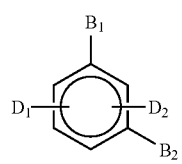

wherein D1 is a radical

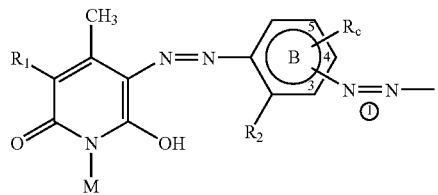

and $B_1$, $B_2$, $D_2$, $R_1$, $R_2$, $R_t$ and M are indicated in Table I below;

TABLE I

| Ex. | $R_1$ | M | $R_2$ | $R_t$ (position on ring B) | Position of the azo ① on ring B | $B_1$ | $B_2$ | $D_2$ |
|---|---|---|---|---|---|---|---|---|
| 3 | —N⁺(C₅H₅) A⁻ | | H | H | 4 | OH | OH | H |
| 4 | " | " | H | H | 4 | OH | OH | $D_1$ |
| 5 | " | " | H | H | 4 | $NH_2$ | $NH_2$ | H |
| 6 | " | " | H | H | 4 | $NH_2$ | $NH_2$ | $D_1$ |
| 7 | " | " | H | H | 4 | $NH_2$ | OH | H |
| 8 | " | H | H | H | 3 | OH | OH | 4 |
| 9 | " | H | H | H | 3 | OH | OH | $D_1$ |
| 10 | " | H | H | H | 3 | $NH_2$ | $NH_2$ | H |
| 11 | " | H | H | H | 3 | $NH_2$ | | $D_1$ |
| 12 | " | H | H | H | 3 | OH | $NH_2$ | |
| 13 | " | H | H | H | 4 | OH | OH | H |
| 14 | " | H | H | H | 4 | OH | OH | $D_1$ |
| 15 | " | H | H | H | 4 | OH | $NH_2$ | H |
| 16 | —N⁺(3-CH₃-C₅H₄) A⁻ | H | H | H | 3 | OH | OH | H |
| 17 | " | H | H | H | 3 | OH | OH | $D_1$ |
| 18 | " | H | H | H | 4 | $NH_2$ | $NH_2$ | H |
| 19 | " | H | H | H | 4 | $NH_2$ | $NH_2$ | $D_1$ |
| 20 | " | H | H | H | 4 | $NH_2$ | OH | H |
| 21 | —N⁺(C₅H₅) A⁻ | —(CH$_2$)$_3$—N(C$_2$H$_5$)$_2$ | H | H | 3 | OH | OH | H |
| 22 | " | " | H | H | 3 | OH | OH | $D_1$ |
| 23 | " | " | H | H | 4 | $NH_2$ | $NH_2$ | H |
| 24 | " | " | H | H | 4 | $NH_2$ | OH | H |
| 25 | " | " | H | H | 4 | OH | OH | H |
| 26 | —CN | " | H | H | 3 | OH | OH | H |
| 27 | " | " | H | H | 3 | OH | OH | $D_1$ |
| 28 | " | " | H | H | 4 | OH | OH | H |
| 29 | " | " | H | H | 4 | OH | $NH_2$ | H |
| 30 | " | " | H | H | 4 | $NH_2$ | $NH_2$ | H |
| 31 | —$CONH_2$ | " | H | H | 3 | OH | OH | H |
| 32 | " | " | H | H | 3 | OH | OH | $D_1$ |
| 33 | " | " | H | H | 4 | $NH_2$ | $NH_2$ | H |
| 34 | H | " | H | H | 3 | OH | OH | H |
| 35 | H | " | H | H | 3 | OH | OH | $D_1$ |
| 36 | H | " | H | H | 4 | $NH_2$ | $NH_2$ | H |
| 37 | H | " | H | H | 4 | $NH_2$ | OH | H |
| 38 | —CN | —(CH$_2$)$_3$N(C$_2$H$_5$)$_2$ | H | H | 3 | OH | OH | H |
| 39 | —$CONH_2$ | " | H | H | 4 | OH | OH | H |
| 40 | H | " | H | H | 4 | $NH_2$ | $NH_2$ | H |

TABLE I-continued

| Ex. | R₁ | M | R₂ | R₁ (position on ring B) | Position of the azo ① on ring B | B₁ | B₂ | D₂ |
|---|---|---|---|---|---|---|---|---|
| 41 | —N⁺(pyridinium) A⁻ | —(CH₂)₃—N(CH₃)₂ | OH | H | 5 | OH | OH | H |
| 42 | " | H | OH | H | 5 | OH | OH | H |
| 43 | " | H | H | OH-(4) | 3 | OH | OH | H |
| 44 | H | —(CH₂)₃—N(CH₃)₂ | OH | H | 5 | OH | OH | H |
| 45 | H | " | H | OH-(4) | 3 | OH | OH | H |
| 46 | H | " | H | H | 4 | OH | OH | H |

wherein R₁, M and Me are indicated in Table 2

TABLE 2

| Ex. | R₁ | M | Me Metal complex |
|---|---|---|---|
| 47 | 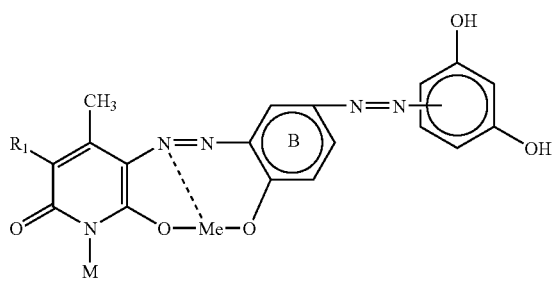—N⁺(pyridinium) A⁻ | —(CH₂)₃—N(CH₃)₂ | 1:1-Cu |
| 48 | " | " | 1:2-Cr |
| 49 | " | " | 1:2-Co |
| 50 | " | " | 1:2-Fe |
| 51 | " | H | 1:1-Cu |
| 52 | " | H | 1:2-Cr |
| 53 | " | H | 1:2-Co |
| 54 | " | H | 1:2-Fe |
| 55 | —N⁺(3-methylpyridinium) A⁻ | H | 1:1-Cu |
| 56 | " | H | 1:2-Fe |
| 57 | H | —(CH₂)₃N(CH₃)₂ | 1:1-Cu |

TABLE 2-continued

| Ex. | R₁ | M | Me Metal complex |
|---|---|---|---|
| 58 | H | " | 1:2-Cr |
| 59 | H | " | 1:2-Co |
| 60 | H | " | 1:2-Fe |

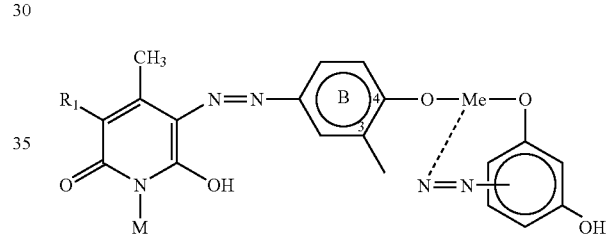

wherein R₁, M and Me are Indicated in Table 3 below;

TABLE 3

| Ex. | R₁ | M | Me Metal complex |
|---|---|---|---|
| 61 | —N⁺(pyridinium) A⁻ | H | 1:1-Cu |
| 62 | " | H | 1:2-Cr |
| 63 | " | H | 1:2-Co |
| 64 | " | H | 1:2-Fe |
| 65 | —N⁺(3-methylpyridinium) A⁻ | H | 1:1-Cu |
| 66 | " | H | 1:2-Fe |
| 67 | H | —(CH₂)₃N(CH₃)₂ | 1:1-Cu |
| 68 | H | " | 1:2-Cr |
| 69 | H | " | 1:2-Co |
| 70 | H | " | 1:2-Fe |

Example 71
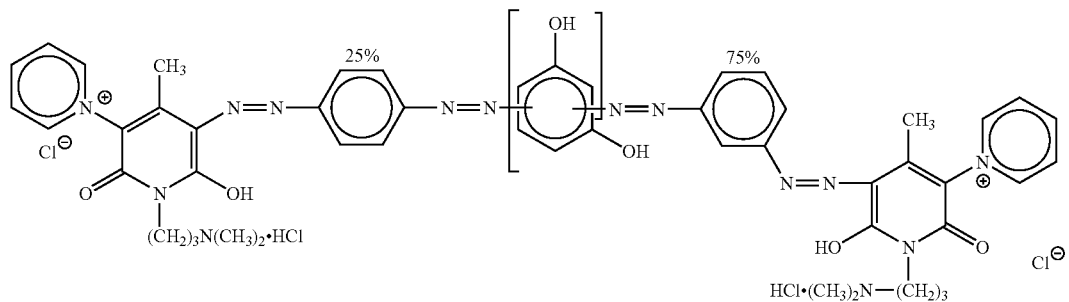
Example 72
Example 72a
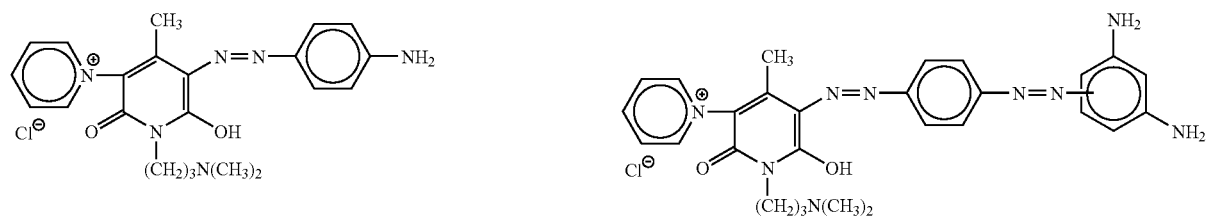
Example 72b
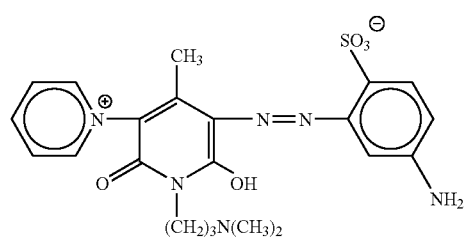
Example 72c
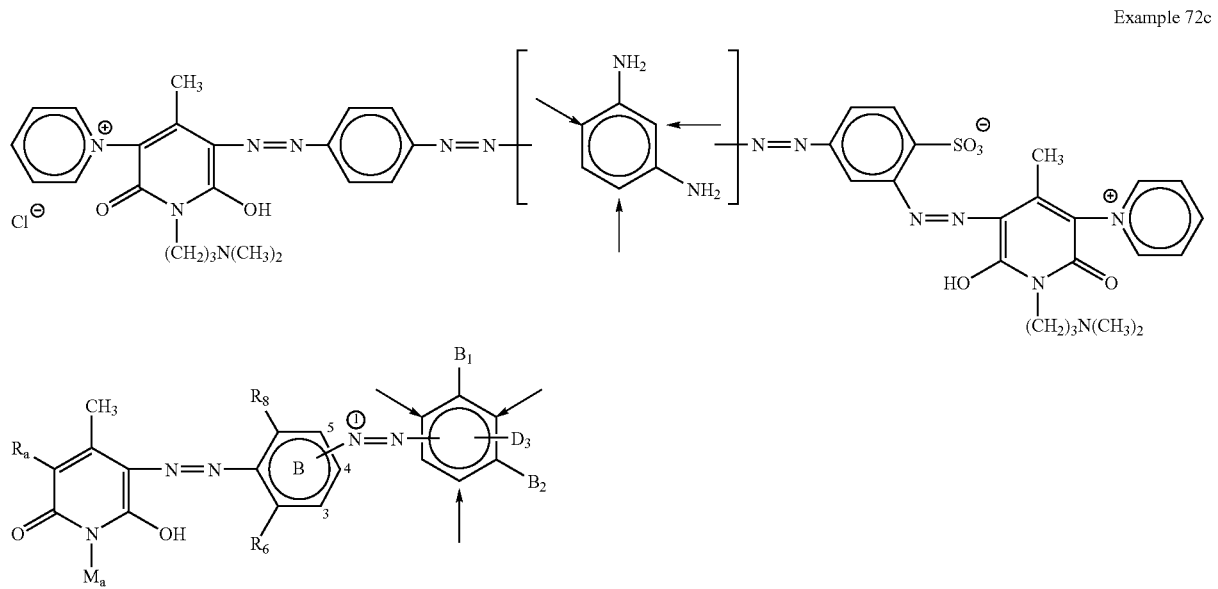

wherein D₃ is hydrogen or a radical of formula

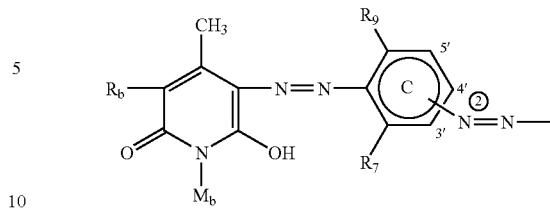

and $B_1$, $B_2$, $R_a$, $R_b$, $R_6$, $R_7$, $R_8$, $R_9$, $M_a$, and $M_b$ are as indicated in Table 4;

TABLE IV

Significances of Ma and Mb $M_1$ is H $M_2$ is —(CH₂)₃N(CH₃)₂

$M_3$ is —(CH₂)₂N(C₂H₅)₂

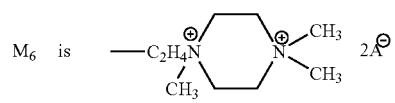

$M_4$ is

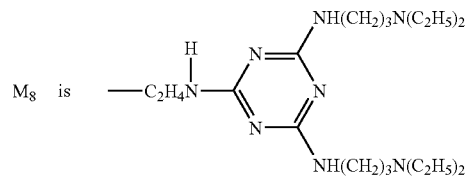

$M_5$ is —C₂H₄—N⟨piperazine⟩N—CH₃

$M_6$ is 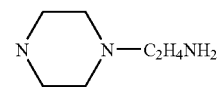

$M_7$ is —(CH₂)₃N⊕(CH₃)₃ A⊖

$M_8$ is (triazine with NH(CH₂)₃N(C₂H₅)₂ substituents)

$M_9$ is (triazine with NH(CH₂)₃N(C₂H₅)₂ and piperazine-C₂H₄NH₂)

$M_{10}$ is —(CH₂)₂NH₂

Significances of Ra and Rb $R_1$ is H $R_2$ is 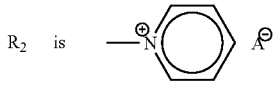

$R_3$ is 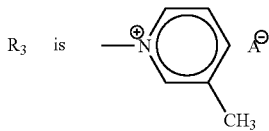

$R_4$ is CN $R_5$ is 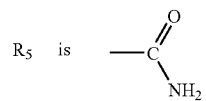

| Ex. | Ra | Ma | R₆ | R₈ | Position of the azo ① on ring B | H or D₃ | R_b | M_b | R₇ | R₉ | Position of the azo ② on ring C | B₁ | B₂ |
|---|---|---|---|---|---|---|---|---|---|---|---|---|---|
| 73 | R₂ | M₂ | SO₃H | H | 3 | H | — | — | — | H | — | OH | OH |
| 74 | R₂ | M₂ | " | H | 4 | H | — | — | — | H | — | OH | NH₂ |
| 75 | R₂ | M₂ | " | H | 4 | H | — | — | — | H | — | NH₂ | NH₂ |
| 76 | R₂ | M₂ | " | H | 3 | D₃ | R₂ | M₂ | SO₃H | H | 3' | NH₂ | NH₂ |

TABLE IV-continued

| | | | | | | | | | | | | |
|---|---|---|---|---|---|---|---|---|---|---|---|---|
| 77 | $R_2$ | $M_2$ | " | H | 3 | $D_3$ | $R_2$ | $M_2$ | H | H | 4' | $NH_2$ | $NH_2$ |
| 78 | $R_2$ | $M_2$ | " | H | 3 | $D_3$ | $R_2$ | $M_2$ | H | H | 4' | $NH_2$ | $NH_2$ |
| 79 | $R_2$ | $M_2$ | " | H | 3 | $D_3$ | $R_2$ | $M_2$ | H | H | 4' | $NH_2$ | OH |
| 80 | $R_2$ | $M_2$ | " | H | 3 | $D_3$ | $R_2$ | $M_2$ | H | H | 4' | OH | OH |
| 81 | $R_2$ | $M_2$ | " | H | 4 | $D_3$ | $R_2$ | $M_2$ | H | H | 3' | $NH_2$ | $NH_2$ |
| 82 | $R_3$ | $M_1$ | H | H | 3 | $D_3$ | $R_2$ | $M_2$ | $SO_3H$ | H | 4' | $NH_2$ | $NH_2$ |
| 83 | $R_1$ | $M_4$ | H | H | 3 | $D_3$ | $R_2$ | $M_5$ | " | H | 4' | OH | $NH_2$ |
| 84 | $R_4$ | $M_4$ | H | H | 3 | $D_3$ | $R_2$ | $M_6$ | " | H | 4' | $NH_2$ | $NH_2$ |
| 85 | $R_5$ | $M_4$ | H | H | 3 | $D_3$ | $R_2$ | $M_7$ | " | H | 4' | $NH_2$ | $NH_2$ |
| 86 | $R_2$ | $M_2$ | $SO_3H$ | H | 4 | $D_3$ | $R_2$ | $M_2$ | H | H | 3' | OH | $NH_2$ |
| 87 | $R_2$ | $M_2$ | " | H | 4 | $D_3$ | $R_2$ | $M_2$ | H | H | 3' | OH | OH |
| 88 | $R_2$ | $M_8$ | " | H | 4 | $D_3$ | $R_2$ | $M_1$ | H | H | 3' | OH | OH |
| 89 | $R_2$ | $M_8$ | " | H | 4 | $D_3$ | $R_2$ | $M_2$ | H | H | 3' | OH | $NH_2$ |
| 90 | $R_2$ | $M_8$ | " | H | 4 | $D_3$ | $R_2$ | $M_4$ | $SO_3H$ | H | 3' | $NH_2$ | $NH_2$ |
| 91 | $R_2$ | $M_9$ | H | H | 4 | $D_3$ | $R_2$ | $M_5$ | $SO_3H$ | H | 3' | OH | $NH_2$ |
| 92 | $R_2$ | $M_9$ | H | H | 3 | $D_3$ | $R_4$ | $M_3$ | " | H | 4' | OH | OH |
| 93 | $R_2$ | $M_8$ | H | H | 3 | $D_3$ | $R_5$ | $M_4$ | " | H | 4' | $NH_2$ | $NH_2$ |
| 94 | $R_2$ | $M_3$ | H | H | 4 | $D_3$ | $R_2$ | $M_3$ | " | H | 3' | $NH_2$ | $NH_2$ |
| 95 | $R_2$ | $M_2$ | H | $CH_3$ | 3 | $D_3$ | $R_2$ | $M_2$ | " | H | 4' | OH | OH |
| 96 | $R_2$ | $M_3$ | H | Cl | 3 | $D_3$ | $R_2$ | $M_3$ | " | H | 4' | $NH_2$ | $NH_2$ |
| 97 | $R_2$ | $M_2$ | H | $OCH_3$ | 3 | $D_3$ | $R_2$ | $M_4$ | " | H | 4' | $NH_2$ | $NH_2$ |
| 98 | $R_2$ | $M_7$ | $SO_3H$ | H | 4 | $D_3$ | $R_2$ | $M_7$ | H | Cl | 3' | OH | OH |
| 99 | $R_2$ | $M_8$ | " | H | 4 | $D_3$ | $R_2$ | $M_2$ | H | $CH_3$ | 3' | OH | $NH_2$ |
| 100 | $R_2$ | $M_6$ | " | H | 4 | $D_3$ | $R_2$ | $M_2$ | H | $OCH_3$ | 3' | $NH_2$ | $NH_2$ |
| 101 | $R_2$ | $M_2$ | " | H | 3 | $D_3$ | $R_2$ | $M_2$ | H | H | 3' | OH | $NH_2$ |
| 102 | $R_2$ | $M_2$ | " | H | 4 | $D_3$ | $R_2$ | $M_2$ | H | H | 4' | $NH_2$ | $NH_2$ |
| 103 | $R_2$ | $M_2$ | " | H | 4 | $D_3$ | $R_2$ | $M_2$ | $SO_3H$ | H | 4' | $NH_2$ | $NH_2$ |
| 104 | $R_2$ | $M_2$ | " | H | 3 | $D_3$ | $R_2$ | $M_2$ | H | H | 3' | $NH_2$ | $NH_2$ |
| 105 | $R_2$ | $M_2$ | " | H | 4 | $D_3$ | $R_2$ | $M_2$ | H | H | 4' | $NH_2$ | OH |
| 106 | $R_2$ | $M_2$ | " | H | 3 | $D_3$ | $R_2$ | $M_2$ | $SO_3H$ | H | 4' | OH | $NH_2$ |
| 107 | $R_2$ | $M_{10}$ | " | H | 3 | $D_3$ | $R_2$ | $M_2$ | H | H | 3' | OH | OH |

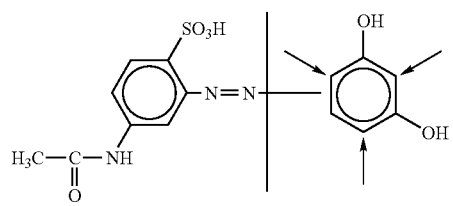

Example 108a

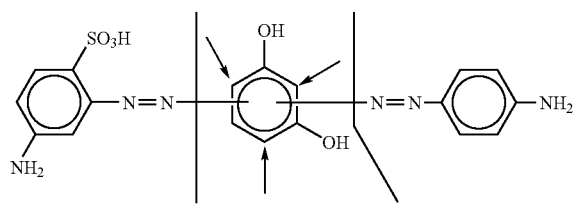

Example 108b

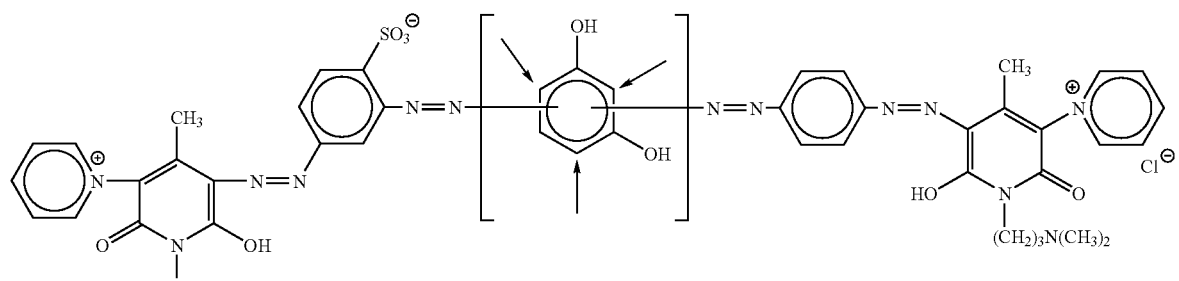

Example 108c

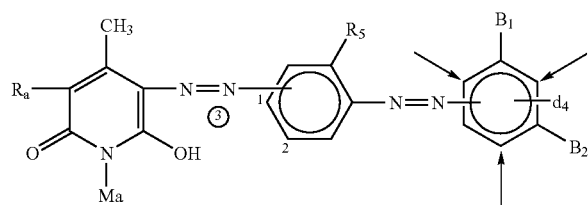

Example 108d wherein d4 is H or D4

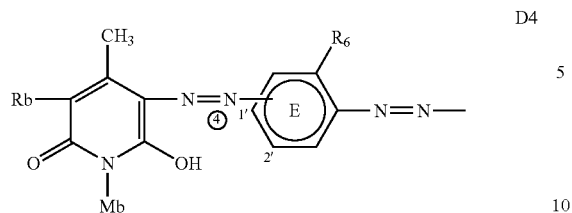

and $R_a$, $R_b$, $R_5$, $R_6$, $B_1$, $B_2$, $M_a$, and $M_b$ are as indicated in Table 5 below;

TABLE V

| Ex. Nr. | Ra | Ma | $R_5$ | Position of the azo ③ on ring D | $d_4$ | $R_b$ | $M_b$ | $R_6$ | Position of the azo ④ on ring E | $B_1$ | $B_2$ |
|---|---|---|---|---|---|---|---|---|---|---|---|
| 109 | $R_2$ | $M_2$ | $SO_3H$ | 1 | H | — | — | — | — | OH | OH |
| 110 | $R_2$ | $M_2$ | " | 1 | H | — | — | — | — | $NH_2$ | $NH_2$ |
| 111 | $R_2$ | $M_2$ | " | 2 | H | — | — | — | — | OH | $NH_2$ |
| 112 | $R_2$ | $M_2$ | " | 2 | H | — | — | — | — | $NH_2$ | $NH_2$ |
| 113 | $R_2$ | $M_2$ | " | 1 | $D_4$ | $R_2$ | $M_2$ | H | 1' | OH | $NH_2$ |
| 114 | $R_2$ | $M_2$ | " | 1 | $D_4$ | $R_2$ | $M_2$ | H | 1' | $NH_2$ | $NH_2$ |
| 115 | $R_2$ | $M_2$ | " | 1 | $D_4$ | $R_2$ | $M_2$ | $SO_3H$ | 1' | OH | OH |
| 116 | $R_2$ | $M_2$ | " | 1 | $D_4$ | $R_2$ | $M_2$ | H | 2' | OH | OH |
| 117 | $R_2$ | $M_2$ | " | 1 | $D_4$ | $R_2$ | $M_2$ | H | 2' | $NH_2$ | $NH_2$ |
| 118 | $R_2$ | $M_2$ | " | 1 | $D_4$ | $R_2$ | $M_2$ | $SO_3H$ | 2' | OH | $NH_2$ |
| 119 | $R_2$ | $M_2$ | " | 2 | $D_4$ | $R_2$ | $M_2$ | " | 2' | OH | OH |
| 120 | $R_3$ | $M_3$ | " | 1 | $D_4$ | $R_3$ | $M_3$ | H | 1' | OH | OH |
| 121 | $R_2$ | $M_4$ | " | 1 | $D_4$ | $R_2$ | $M_4$ | H | 2' | $NH_2$ | $NH_2$ |
| 122 | $R_2$ | $M_5$ | H | 1 | $D_4$ | $R_2$ | $M_5$ | $SO_3H$ | 2' | $NH_2$ | OH |
| 123 | $R_2$ | $M_5$ | H | 2 | $D_4$ | $R_2$ | $M_6$ | " | 1' | OH | OH |
| 124 | $R_3$ | $M_7$ | H | 2 | $D_4$ | $R_3$ | $M_7$ | " | 1' | $NH_2$ | OH |
| 125 | $R_1$ | $M_8$ | $SO_3H$ | 2 | $D_4$ | $R_1$ | $M_8$ | " | 1' | OH | OH |
| 126 | $R_1$ | $M_8$ | " | 2 | $D_4$ | $R_1$ | $M_8$ | H | 1' | $NH_2$ | $NH_2$ |
| 127 | $R_2$ | $M_9$ | " | 1 | $D_4$ | $R_2$ | $M_9$ | H | 2' | OH | $NH_2$ |
| 128 | $R_2$ | $M_2$ | " | 2 | $D_4$ | $R_2$ | $M_2$ | H | 1' | OH | OH |
| 129 | $R_2$ | $M_2$ | H | 2 | $D_4$ | $R_2$ | $M_2$ | $SO_3H$ | 1' | OH | OH |
| 130 | $R_2$ | $M_2$ | $SO_3H$ | 2 | $D_4$ | $R_2$ | $M_2$ | H | 1' | $NH_2$ | $NH_2$ |
| 131 | $R_2$ | $M_2$ | H | 2 | $D_4$ | $R_2$ | $M_2$ | $SO_3H$ | 1' | $NH_2$ | $NH_2$ |
| 132 | $R_2$ | $M_2$ | $SO_3H$ | 2 | $D_4$ | $R_2$ | $M_2$ | " | 1' | $NH_2$ | $NH_2$ |
| 133 | $R_2$ | $M_2$ | " | 1 | $D_4$ | $R_2$ | $M_2$ | " | 1' | $NH_2$ | $NH_2$ |
| 134 | $R_2$ | $M_2$ | H | 2 | $D_4$ | $R_2$ | $M_2$ | " | 1' | OH | $NH_2$ |
| 135 | $R_2$ | $M_2$ | $SO_3H$ | 2 | $D_4$ | $R_2$ | $M_2$ | " | 1' | OH | $NH_2$ |
| 136 | $R_2$ | $M_2$ | " | 1 | $D_4$ | $R_2$ | $M_2$ | " | 1' | OH | $NH_2$ |

Example 137a

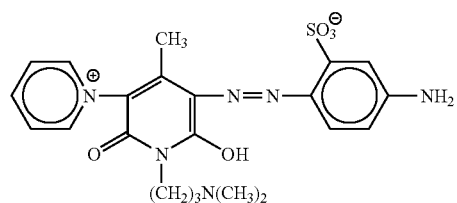

Example 137b

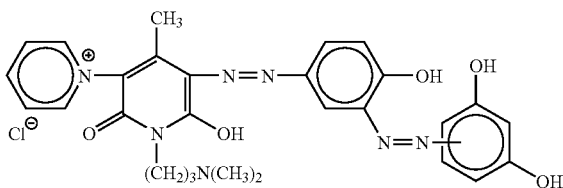

Example 137c

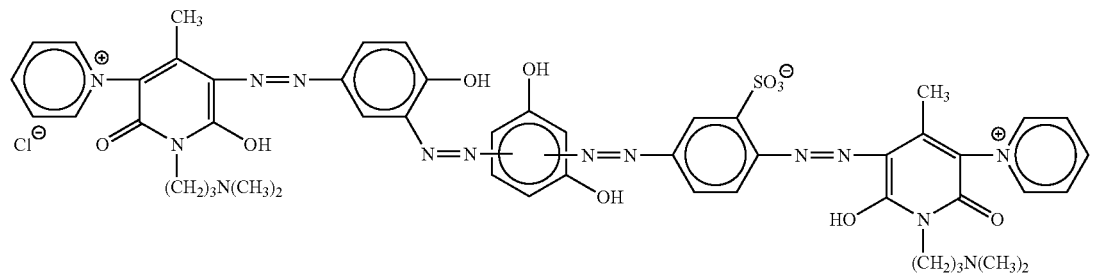

Example 137d

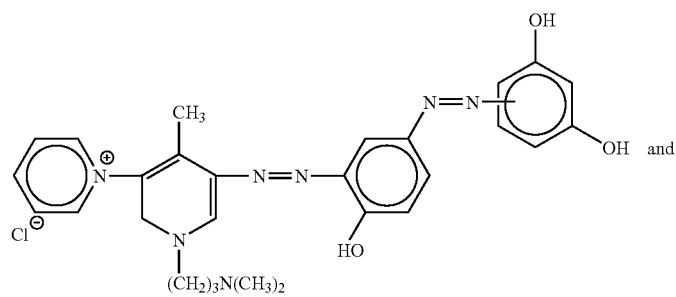

and

Example 137e

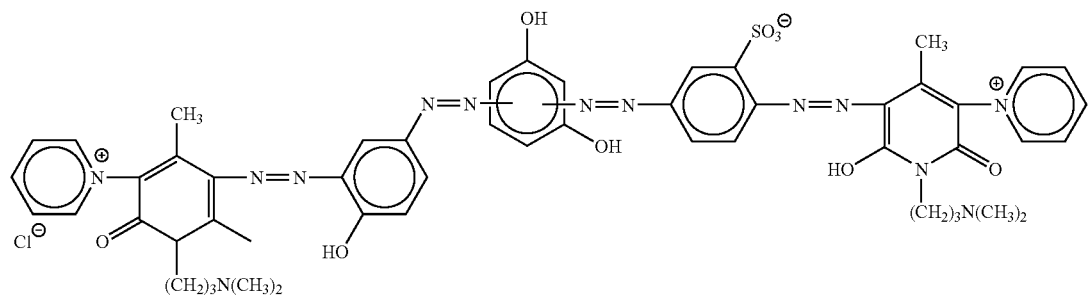

and a dye selected from the group consisting of: C.I. Basic Brown 23; C.I. Basic Red 12; C.I. Basic Blue 1; CA. Basic Red 14; C.I. Basic Violet 10; and C.I. Basic Blue 26; in an amount to have 100 parts in total as component two.

7. A process for dyeing or printing fiber material or dyeing or printing paper comprising the steps of:
providing a dye or printing paste comprising a compound according to claim 1;
providing a fiber material or paper; and
contacting said dye or printing paste with said fiber material or paper.

8. A material dyed or printed with compounds according to claim 1.

9. An ink-jet ink comprising a compound according to claim 1.

10. A process for the preparation of an ink-jet ink comprising the step of: adding a compound according to claim 1 to at least one other compound.

11. A process for the preparation of an azo compound of formula (I) according to claim 1 comprising: reacting the diazonium salt of a compound according to formula (II)

$$\left[\begin{array}{c}\text{NH}_2\\ \phantom{x}\\ \text{C}-\text{A}-\text{CH}_2\end{array}\right]_n\!\!\!-\!\!\text{B}\!-\!(\text{CH}_2\text{OH})_m \quad \text{(II)}$$

or mixtures of such diazonium salts with a suitable coupling component comprising moieties of formula CC or with a mixture of suitable coupling components comprising moieties of formula CC wherein B and the moiety CC have the meaning as defined in claim 1.

12. A compound according to formula (II)

$$\left[\begin{array}{c}\text{NH}_2\\ \phantom{x}\\ \text{C}-\text{A}-\text{CH}_2\end{array}\right]_n\!\!\!-\!\!\text{B}\!-\!(\text{CH}_2\text{OH})_m, \quad \text{(II)}$$

wherein
B is
—[—(CH$_2$)$_{1-4}$—O—(CH$_2$)$_{1-4}$]$_4$C or
[—(CH$_2$)$_{1-3}$—O—CH$_2$)$_{1-3}$—O—(CH$_2$)$_{1-3}$]$_4$C or
[—(CH$_2$)$_{1-2}$—O—(CH$_2$)$_{1-2}$—O—(CH$_2$)$_{1-2}$]$_4$C or
[(—CH$_2$)$_{1-4}$]$_2$N(CH$_2$)$_{1-4}$N[(—CH$_2$)$_{1-4}$]$_2$
A is independently —NH— or —O—
m and n are natural numbers
with the provisos that
(i) the sum of n and m is smaller as or equal to the valencies of B,
(ii) when n=2 then m is $\geq$1,
(iii) when n=3 and A=NH then m is $\geq$1,
and their salts and/or mixtures thereof.

13. A compound according to claim 12 wherein A is —O—.

14. A material dyed or printed with at least one mixture according to claim 4.

15. A material dyed or printed with at least one mixture according to claim 5.

16. An ink-jet ink comprising a mixture according to claim 4.

17. An ink-jet ink comprising a mixture according to claim 5.

18. A compound of formula (Ia)

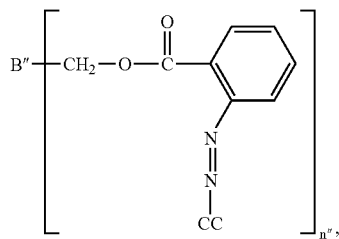

wherein
CC is a moiety of formula (a$_1$) or (c$_2$),

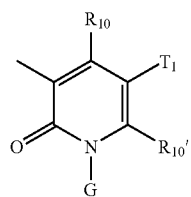

wherein
R$_{10}$ is H; —CH$_3$ or —CH$_2$CH$_3$,
T$_1$ is H; —CN; —CONH$_2$; —CONHCH$_3$;

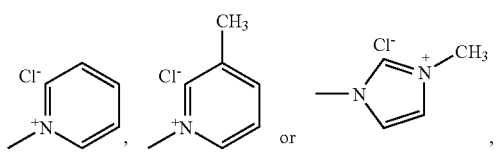

R$_{10}$' is H; —CH$_3$ or —OH,
G is H or —(CH$_2$)$_{2-4}$NR$_{13}$R$_{14}$, wherein R$_{13}$ and R$_{14}$ are independently from each other H; —CH$_3$ or —CH$_2$CH$_3$, or

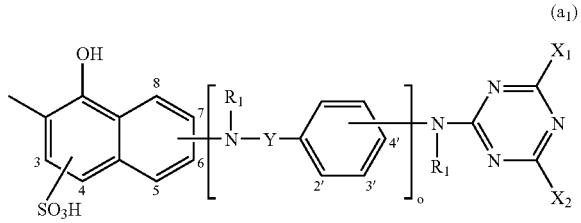

wherein
each R$_1$ is independently from each other H; —CH$_3$, —CH$_2$CH$_3$ or substituted C$_{1-4}$alkyl,
X$_1$ and X$_2$ are independently from each other halogen or —NR$_2$R$_3$
wherein R$_2$ and R$_3$ are independently from each other H; C$_{1-4}$alkyl;
—C$_{2-4}$alkylene-NH$_2$— or —C$_{2-4}$alkylene-OH—,
Y is a direct bond;

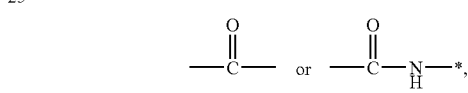

wherein the asterisk is the bond to the benzene ring and
o is 0 or 1
n" is 1, 2, 3 or 4, with the provisos that
when n" is 1 then B" is C(CH$_2$OH)$_3$
when n" is 2 then B" is C(CH$_2$OH)$_2$
when n" is 3 then B" is C(CH$_2$OH)
when n" is 4 then B" is
C; [—(CH$_2$)$_{1-4}$—O—(CH$_2$)$_{1-4}$]$_4$C; [—(CH$_2$)$_{1-3}$—O—(CH$_2$)$_{1-3}$—O—(CH$_2$)$_{1-3}$]$_4$C;
[—(CH$_2$)$_{1-2}$—O—(CH$_2$)$_{1-2}$—O—(CH$_2$)$_{1-2}$—O—(CH$_2$)$_{1-2}$]$_4$C or [(—CH$_2$)$_{1-4}$]$_2$N(CH$_2$)$_{1-4}$N[(—CH$_2$)$_{1-4}$]$_2$.

19. A mixture comprising:
at least one compound of formula (Ia) according to claim 18 wherein B" is C(CH$_2$OH)$_3$ and n" is 1,
at least one compound wherein B" is C(CH$_2$OH)$_2$ and n" is 2,
at least one compound of formula (Ia) wherein B" is C(CH$_2$OH) and n" is 3,
and at least one compound of formula (Ia) wherein B" is C and n" is 4.

20. A mixture comprising at least one compound of formula (Ia) of claim 18.

21. A process for dyeing or printing fiber material or dyeing or printing paper comprising the steps of:
providing a dye or printing paste comprising a compound according to claim 18;
providing a fiber material or paper; and
contacting said dye or printing paste with said fiber material or paper.

22. A material dyed or printed with at least one compound according to claim 18.

23. A material dyed or printed with at least one mixture according to claim 20.

24. An ink-jet ink comprising at least one compound according to claim 18.

25. An ink-jet ink comprising at least one mixture according to claim 20.

26. A process for the preparation of an ink-jet ink comprising the step of:

adding a compound according to claim 18 to at least one other compound.

27. A process for the preparation of an ink-jet ink comprising the step of:

adding a mixture according to claim 20 to at least one other compound.

* * * * *